United States Patent
Francis et al.

(10) Patent No.: US 11,524,290 B2
(45) Date of Patent: Dec. 13, 2022

(54) DISCRETE VOLUME DISPENSING SYSTEM FLOW RATE AND ANALYTE SENSOR

(71) Applicants: University Of Cincinnati, Cincinnati, OH (US); Eccrine Systems, Inc., Cincinnati, OH (US)

(72) Inventors: Jessica Francis, New Vienna, OH (US); Mikel Larson, Cincinnati, OH (US); Michelle D. Hoffman, Wyoming, OH (US); Eliot Gomez, Cincinnati, OH (US); Jason Charles Heikenfeld, Cincinnati, OH (US); Isaac Stamper, Morrow, OH (US)

(73) Assignees: University Of Cincinnati, Cincinnati, OH (US); Eccrine Systems, Inc., Cincinnati, OH (US)

( * ) Notice: Subject to any disclaimer, the term of this patent is extended or adjusted under 35 U.S.C. 154(b) by 177 days.

(21) Appl. No.: 16/649,211

(22) PCT Filed: Sep. 21, 2018

(86) PCT No.: PCT/US2018/052176
§ 371 (c)(1),
(2) Date: Mar. 20, 2020

(87) PCT Pub. No.: WO2019/060689
PCT Pub. Date: Mar. 28, 2019

(65) Prior Publication Data
US 2020/0298231 A1    Sep. 24, 2020

Related U.S. Application Data

(60) Provisional application No. 62/639,018, filed on Mar. 6, 2018, provisional application No. 62/561,335, filed on Sep. 21, 2017.

(51) Int. Cl.
*B01L 3/00* (2006.01)
*A61B 5/145* (2006.01)

(52) U.S. Cl.
CPC .... *B01L 3/502715* (2013.01); *A61B 5/14507* (2013.01)

(58) Field of Classification Search
CPC .. B01L 3/502715; B01L 3/5027; B01L 3/502; B01L 3/50; A61B 5/14507; A61B 5/145; A61B 5/00
(Continued)

(56) References Cited

U.S. PATENT DOCUMENTS

| | | | | |
|---|---|---|---|---|
| 4,994,238 A | * | 2/1991 | Daffern | C12Q 1/54 422/422 |
| 6,352,514 B1 | * | 3/2002 | Douglas | A61B 5/150068 600/583 |

(Continued)

FOREIGN PATENT DOCUMENTS

WO    WO 2016/049019 A1 *    3/2016    ............... A61B 5/00

OTHER PUBLICATIONS

International Searching Authority, European Patent Office, International Search Report and Written Opinion issued in corresponding PCT Application No. PCT/US2018/052176, dated Feb. 20, 2019 (21 pages).

*Primary Examiner* — Christine T Mui
(74) *Attorney, Agent, or Firm* — Wood Herron & Evans LLP

(57) ABSTRACT

A device for determining the amount or concentration of an analyte in a fluid sample and a flow rate of the fluid sample in a channel is provided. The device includes a chamber including a channel and an opening the channel in fluid communication with the opening. The device further includes a wicking component positioned adjacent to the (Continued)

opening configured to receive an amount of fluid from the channel. The device may further include an analyte sensor positioned on the wicking component, the analyte sensor configured to detect an analyte in fluid in contact with the analyte sensor, wherein the wicking component is configured to contact the amount of fluid with the analyte sensor. Alternatively the device may include at least one pair of electrodes configured to determine a flow rate of the fluid in the channel.

9 Claims, 12 Drawing Sheets

(58) Field of Classification Search
USPC .................................................. 422/502, 500
See application file for complete search history.

(56) References Cited

U.S. PATENT DOCUMENTS

| 6,455,324 B1 | 9/2002 | Douglas |
| 2011/0076690 A1 | 3/2011 | Gumbrecht et al. |
| 2013/0224775 A1 | 8/2013 | Davis et al. |

* cited by examiner

DISCRETE VOLUME DISPENSING SYSTEM FLOW RATE AND ANALYTE SENSOR

CROSS-REFERENCE TO RELATED APPLICATIONS

This application is a national stage application under 35 U.S.C. § 371 of International Application No. PCT/US2018/052176, filed on Sep. 21, 2018, which claims the benefit of U.S. Provisional Application No. 62/639,018 filed Mar. 6, 2018, and U.S. Provisional Application No. 62/561,335 filed Sep. 21, 2017 the disclosures of which are hereby incorporated by reference herein in their entireties.

STATEMENT REGARDING FEDERALLY SPONSORED RESEARCH OR DEVELOPMENT

This invention was made with government support under FA8650-16-C-6760 awarded by AFMCLO/JAZ. The government has certain rights in the invention.

BACKGROUND

Most sensors for microfluidic and lab-on-chip systems operate with volumes and flow rates that are optimized for sensors. At very low volumes and flow rates (which can vary depending on the sensor type but typically at or below 1 µL and 20 µL/min, respectively), measurements from the sensors become inaccurate due to several confounding issues that include, but are certainly not limited to, the following: analyte depletion of the sample, electromagnetic interferences, increased impedance between the electrodes, low signal-to-noise ratio, and inconsistent flow rates.

The analyte depletion of the sample is a challenge since electrochemical sensors are especially sensitive to the local fluctuations of an analyte, which can cause false low readings. Enzymatic-based biosensors typically consume the analyte of interest to produce a byproduct (or mediator) that can be detected with an electrode. For example, as shown in FIG. 1, glucose sensors commonly use glucose oxidase (GOx) to catalyze glucose and produce hydrogen peroxide. The hydrogen peroxide can be sensed directly by an electrode when an electric potential is applied (e.g., 0.6 V). In the process, however, glucose is converted to gluconolactone, and the amount of glucose in the sample will reduce over time. Analyte consumption is not a problem for large sample volumes (e.g., greater than 100 µL) or single-use systems. However, when the sample volume is small, the analyte will deplete quickly over time, and the concentration will appear to decrease if a fresh solution is not delivered to the sensor.

Similarly, inconsistent flow rates create a challenge for sensors since the analyte supply rate fluctuates the apparent local concentration. As a result, continuous monitoring systems require high flow rates (e.g., greater than 20 µL/min) and large volumes to sustain accurate analyte levels. Such high flow rates are simply not possible for some biofluids (e.g., sweat, tears, etc.) with very small supply rates (e.g., less than 2 µL/min).

The other problems listed (signal-to-noise, electromagnetic interferences, and increased impedance) are difficult to overcome for any sensor (even beyond electrochemical sensors). These issues are challenging, especially for wearable sweat sensing devices, where the flow rate is 0.1-10 nL/min/gland resulting in a low volume of fluid over time. A need exists for improved methods and systems for sensors with low flow rates or low sample volumes to provide accurate flow rates, fluid dispensing, and/or sensing modalities.

The objects and advantages of the disclosed invention will be further appreciated in light of the following detailed descriptions and drawings.

DETAILED DESCRIPTION OF THE INVENTION

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

Certain embodiments of the disclosed invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a biofluid sensor; an impedance sensor; a sample volume sensor; a sample generation rate sensor; and a solute generation rate sensor. Certain embodiments of the disclosed invention show sub-components of what would be sensing devices with more sub-components needed for use of the device in various applications, which are obvious (such as a battery), and for purposes of brevity and focus on inventive aspects, such components are not explicitly shown in the diagrams or described in the embodiments of the disclosed invention. As a further example, many embodiments of the disclosed invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the scope of the disclosed invention.

Figure 2:
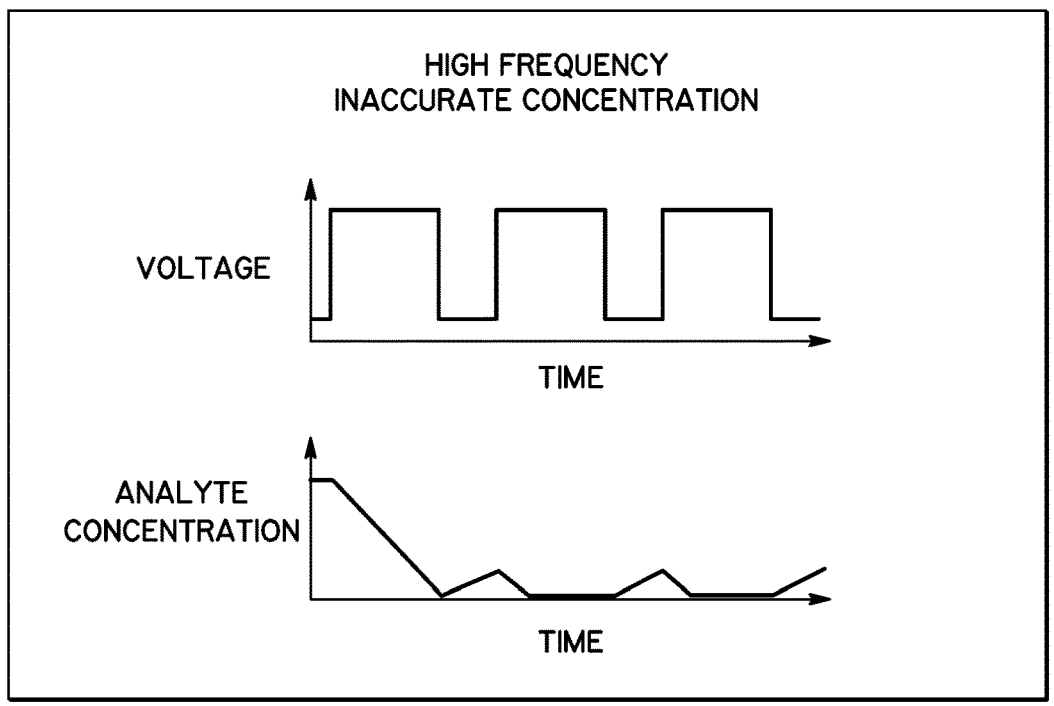
FIG. 2 shows graphs of voltage and analyte concentration versus time from an electrode with a high frequency sampling rate.
Figure 3:
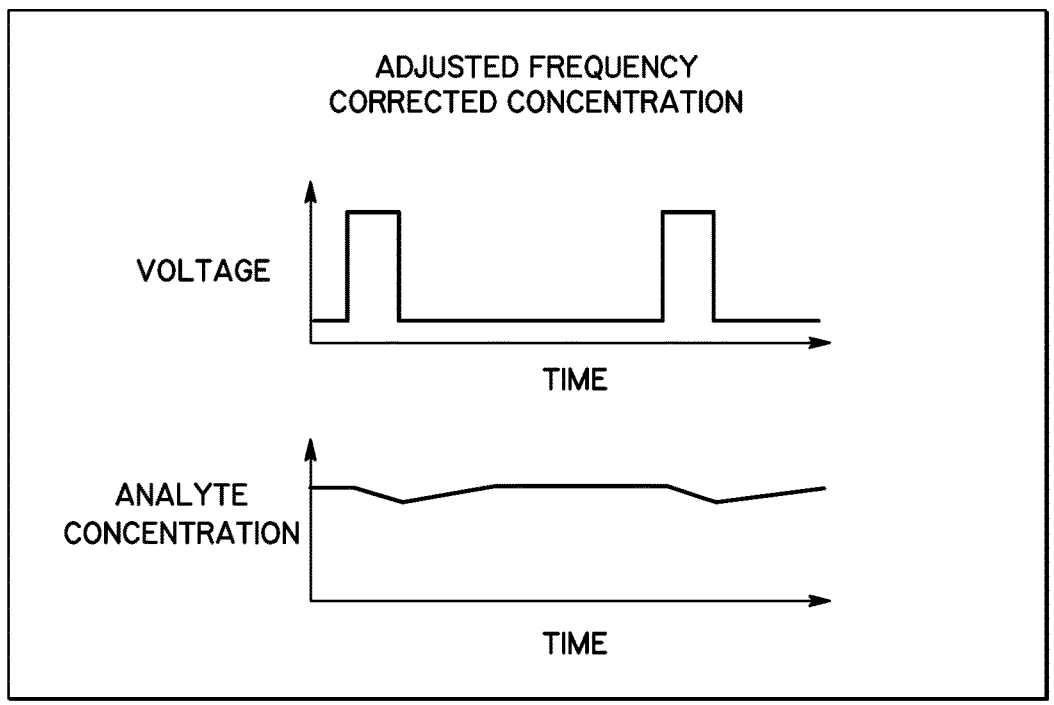
FIG. 3 shows graphs of voltage and analyte concentration versus time from an electrode with a low frequency sampling rate.

Embodiments of the disclosed invention are directed to methods and devices for measuring an analyte, such as glucose, or the fluid flow rate in a continuous system by digitized sampling irrespective of variability in flow rate or volume size. The digitized sampling includes (1) electrical pulses and/or (2) a discrete volume dosing system. Digitized sampling according to the disclosed invention allows for accurate measurement of an analyte concentration when there is a low flow rate and/or volume size. For example, FIG. 2 shows a high frequency of pulses that provides an inaccurate concentration measurement at a slow flow rate. FIG. 3 shows an adjusted frequency of pulses that provides a more accurate or corrected concentration at the same flow rate. The pulse duration ($t_d$) depends on the fluid volume, requiring a shorter pulse for smaller volumes or supply rates (flow rate of the sample to the sensor). As an example, the pulse duration may be less than 10 seconds when the volume is less than 20 µL/min and the supply rate is 1 µL/min. The pulse time will vary as the flow rate increases or decreases.

Figure 1:
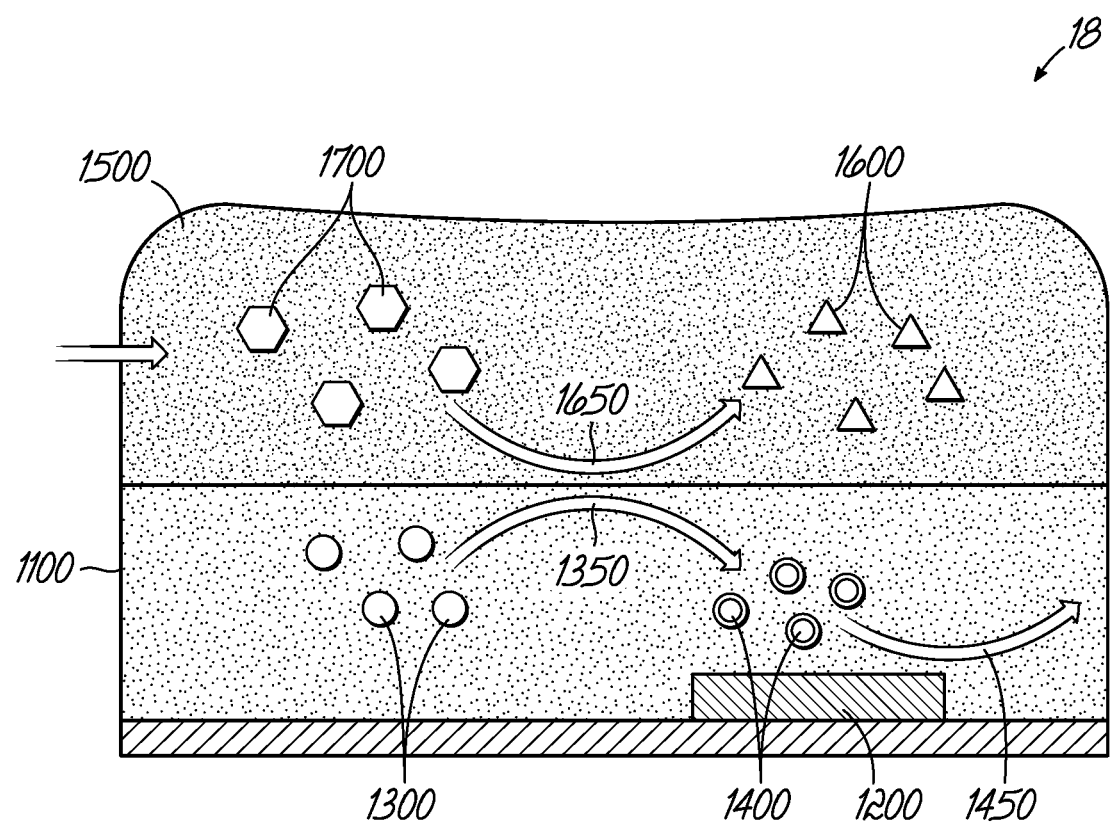
FIG. 1 is a schematic mechanism of an enzymatic glucose sensor showing the consumption of glucose and hydrogen peroxide.

In an embodiment, short electrical pulses (<500 ms) shorten the amount of the mediator or catalyzed product (e.g., hydrogen peroxide) that is reduced/oxidized by the electrode based on the mechanism shown in FIG. 1. The frequency of the pulses may be adjusted based on the flow rate of the target analyte. Short sampling ensures that not all of the mediator is consumed, and slower flow rates of the target analyte support the consumption rate of the mediator. If the flow rate is known using a flow meter, the frequency or duration of electrical pulses can be adjusted accordingly in software if the flow rate changes.

With reference to FIG. 1, a schematic mechanism of an enzymatic-based, analyte biosensor 18 is shown. The analyte biosensor 18 measures a property of a biofluid 1500 in contact with the biosensor 18 by enzymatically reacting an analyte 1700 in the biofluid 1500 with a reactant 1300 in the presence of an enzyme 1100 to form a detectable product 1400. The enzyme 1100 may be encapsulated in a matrix, for example, a hydrogel. The detectable product 1400 can be sensed by an electrode 1200 included in the biosensor 18. For example, the biofluid 1500 may include sweat and the property of the biofluid 1500 may be, for example, the concentration or amount of the analyte 1700 in the biofluid 1500. In some examples, the analyte 1500 includes glucose. An enzyme 1100, such as glucose oxidase (GOx), may catalyze a conversion reaction between the reactant 1300 and the analyte 1700 to form 1350 a byproduct 1600 and form 1350 a detectable product 1400. In an embodiment, the reactant 1300 includes oxygen molecules, the analyte 1700 includes glucose, the enzyme 1100 includes glucose oxidase, the byproduct 1600 includes gluconolactone, and the detectable product 1400 includes hydrogen peroxide. The detectable product 1400 can be sensed 1450 directly by the electrode 1200 when an electric potential is applied (e.g., 0.6 V).

Figure 4A:
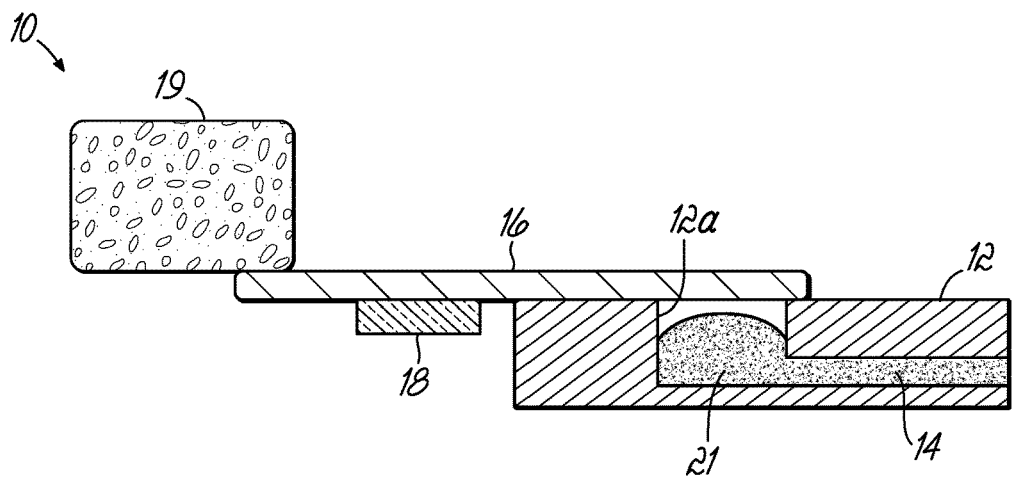
FIG. 4A is a schematic cross-sectional view of a device according to an embodiment of the disclosed invention.
Figure 4B:
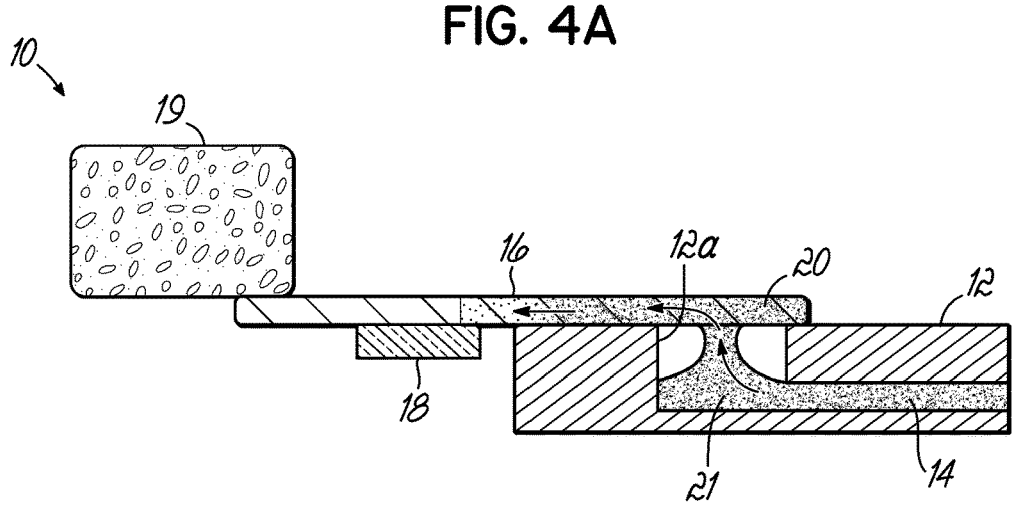
FIG. 4B is a schematic cross-sectional view of the device of FIG. 4A after the fluid contacts the wicking component.
Figure 4C:
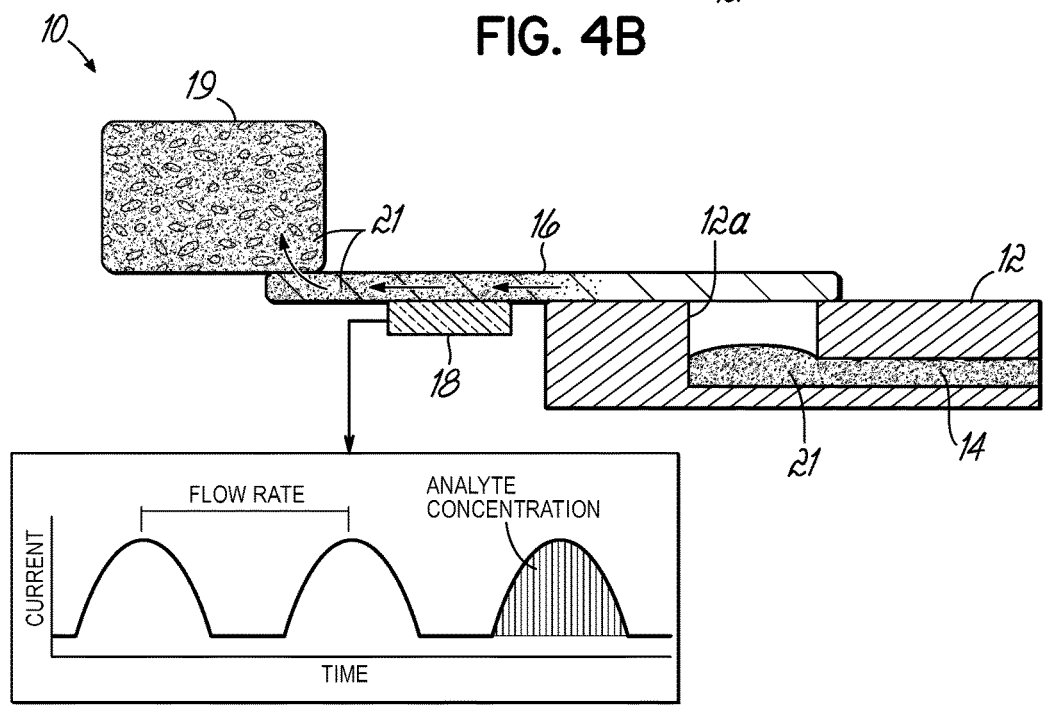
FIG. 4C is a schematic cross-sectional view of the device of FIG. 4A after the discrete sample of fluid has entered the wicking component and a graph of the current versus time over a sampling period.

With reference to FIGS. 4A-4C, in an embodiment, a discrete volume dosing system comprises a biofluid sensing device 10, which is a closed or sealed system in which discrete, quantized samples of fluid 21 are delivered, analyzed, and calibrated independent of flow rate. The discrete, quantized samples have a fixed volume of fluid 21. The discrete, quantized samples are dispensed at an interval based at least in part on the rate at which the amount of fluid 21 in the channel 14 meets or exceeds a threshold volume, however, the volume of the sample taken from the fluid 21 in the channel 14, is independent of the flow rate of fluid 21 in the channel 14. The device 10 includes a fluid-impermeable chamber 12 that includes an opening 12a. The chamber 12 may be made of, for example, acrylic. The chamber 12 defines the fluid channel 14, which may be coated with a hydrophobic material (e.g., Teflon or silica nano-coatings). The channel 14 is designed to receive a continuous, pressure-driven flow of sample fluid 21. The sample fluid 21 travels through the channel 14 towards the opening 12a. The device 10 further includes a wicking component 16 (e.g., Rayon or polyester fibers, sodium polyacrylate, cellulose, etc.) at least a portion of which is adjacent to the opening 12a of the chamber 12. The wicking component 16 transports fluid 21 from the channel 14 to the enzymatic-based, analyte biosensor 18. A pump 19 is in fluidic contact (e.g., physical contact) with the wicking component 16 and aids in drawing the sample fluid 21 through the wicking component 16 and across the analyte sensor 18. Suitable materials for the pump 19 include sodium polyacrylate or a wicking material (e.g., Rayon or polyester fibers, sodium polyacrylate, cellulose, etc.).

As shown in FIG. 4A, because of the hydrophobic coating, a convex meniscus forms. As more fluid 21 enters the channel 14, the convex meniscus moves towards and eventually contacts the wicking component 16. Referring to FIGS. 4B and 4C, when the meniscus contacts the wicking component 16, spontaneous capillary flow occurs and a droplet of the sample fluid 21 enters the wicking component 16. As the droplet of the sample fluid 21 travels through the wicking component 16, the fluid 21 in the channel 14 loses contact with the wicking component 16. The meniscus contacts the wicking component 16 only when the threshold volume is reached in the channel 14. The volume of the droplet depends on several factors, but primarily depends on (1) the height between the chamber 12 or the opening 12a and the wicking component 16 and (2) the radius of the opening 12a (see FIG. 6). Other factors include, for example, contact angle, shape of the opening 12a, and gravity. As more fluid enters the channel 14, the process is repeated. The device 10 is flow rate independent (i.e., flow rate can vary or even be erratic), however the sample fluid 21 only enters and moves through the wicking component 16 and past the analyte sensor 18 when the threshold volume of fluid 21 in the channel 14 is reached or exceeded. Once the volume of fluid 21 in the channel 14 meets or exceeds the threshold volume, the wicking component 16 transports a series of discrete, quantized samples of the fluid 21 across the analyte sensor 18. There is a reaction area adjacent the analyte sensor 18 in which all or a part of the analyte is consumed or reacted (e.g., like the reaction of glucose in FIG. 1). As each discrete sample contacts and passes over the analyte sensor 18, the measured current will increase rapidly and then decrease as the analyte is consumed in the fluid by the sensor 18 or as the fluid 21 flows away from the sensor 18 (FIG. 4C). In an embodiment, the concentration of the analyte is measured by the area under the current versus time curve and compared to calibration results determined by wicking speed and volume delivered to the sensor 18. In addition, the flow rate of the sample over the sensor 18 is calculated by measuring the periodicity of each sample. Advantageously, the volume of the sample fluid 21 does not necessarily vary with the orientation of the device 10.

In an aspect of the disclosed invention, the concentration of the analyte is accurately measured (i.e., the area under the curve) for continuous flow systems. In addition to concentration, the flow rate of the sample is also directly sampled by measuring the periodicity of each sample in each rise in current for each time a quantum of fluid is received.

Sensors are improved by volumetric dispensing of fluid 21 samples and/or digitized sample to ensure that ample fluid 21 is supplied to the sensor.

In an aspect of the disclosed invention, the fluid 21 supply to the analyte sensor 18 may be actively pumped (e.g., via a syringe) or passively generated (e.g., via fluid build-up). For example, the device 10 includes passive, spontaneous capillary flow to provide samples of the fluid 21 to the analyte sensor 18. In an embodiment, a discrete volume dosing system with active fluid 21 supply may include an additional sensor (not shown) that detects when a sufficient amount of fluid 21 is present and a pump (not shown) that dispenses a sample of the fluid 21 accordingly.

With reference to FIGS. 5A-5D, in another embodiment, a discrete volume dosing system with active fluid supply is shown. The discrete volume dosing system includes a device 20 that may be sealed to the skin 200 (e.g., through tape or other adhering techniques). The device 20 includes a fluid-impermeable chamber 22 that includes an opening 22a. The chamber 22 defines a fluid reservoir 24, which may be coated with a hydrophobic material. In the illustrated embodiment, the fluid reservoir 24 is made of one or more layers of a wicking material (e.g., Rayon or polyester fibers, sodium polyacrylate, cellulose, etc.). The chamber 22 may be made of, for example, acrylic. The device 20 further includes a wicking component 26 that transports fluid from the reservoir 24 to an analyte sensor 28. At least a portion of the wicking component 26 is proximate to the opening 22a of the chamber 22. In some examples, the wicking component is positioned no more than 1 cm from the opening and no less than 1 µm from the opening 22a, and the opening 22a has a diameter of no more than 1 cm and no less than 1 µm. The reservoir 24 is designed to receive a flow of biofluid, such as sweat, from the skin 200, for example from sweat glands 210.

Figure 5A:
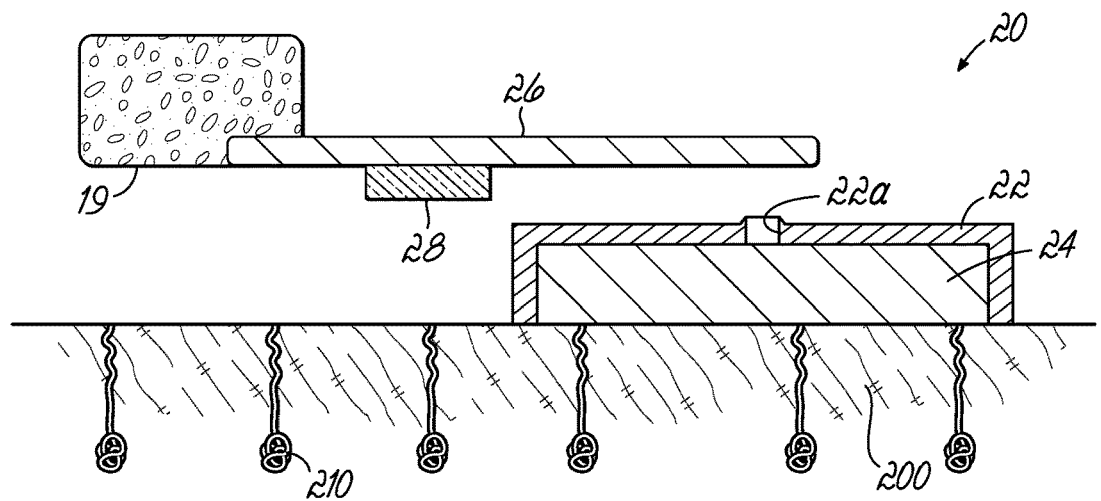
FIG. 5A is a schematic cross-sectional view of a device according to an embodiment of the disclosed invention.
Figure 5B:
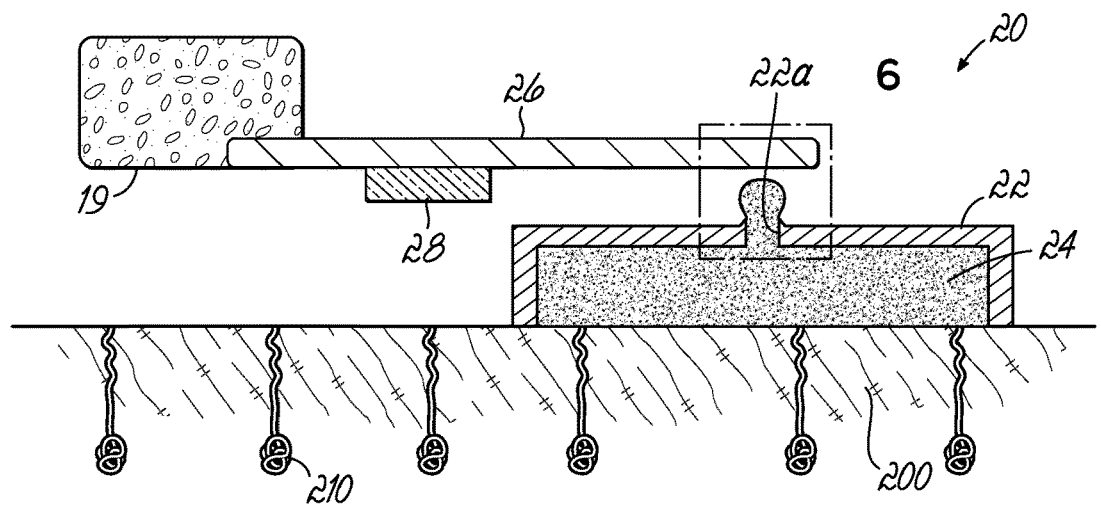
FIG. 5B is a schematic cross-sectional view of the device of FIG. 5A after fluid emerges from the opening of the chamber.
Figure 5C:
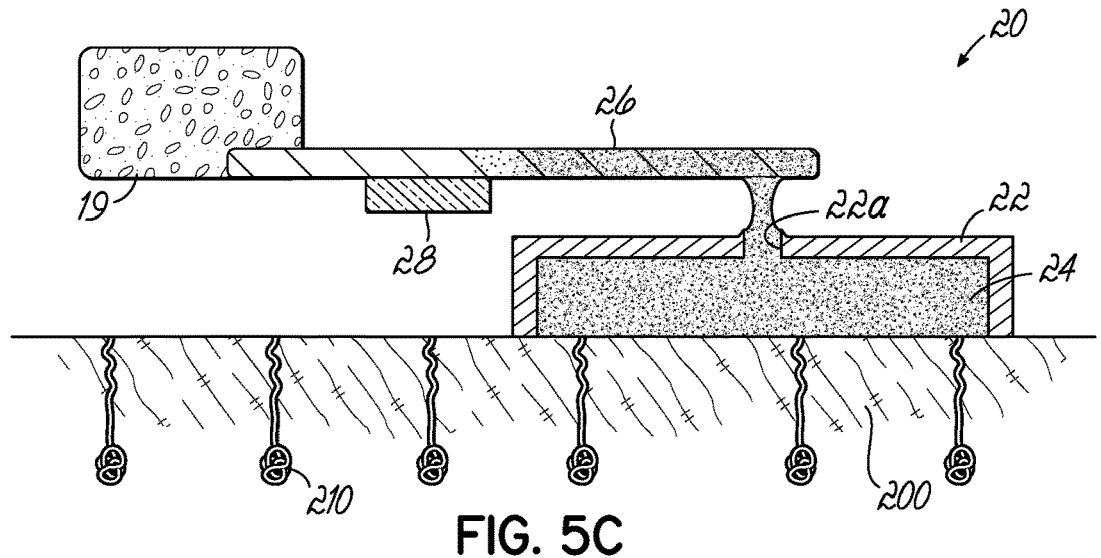
FIG. 5C is a schematic cross-sectional view of the device of FIG. 5A after the fluid contacts the wicking component.
Figure 5D:
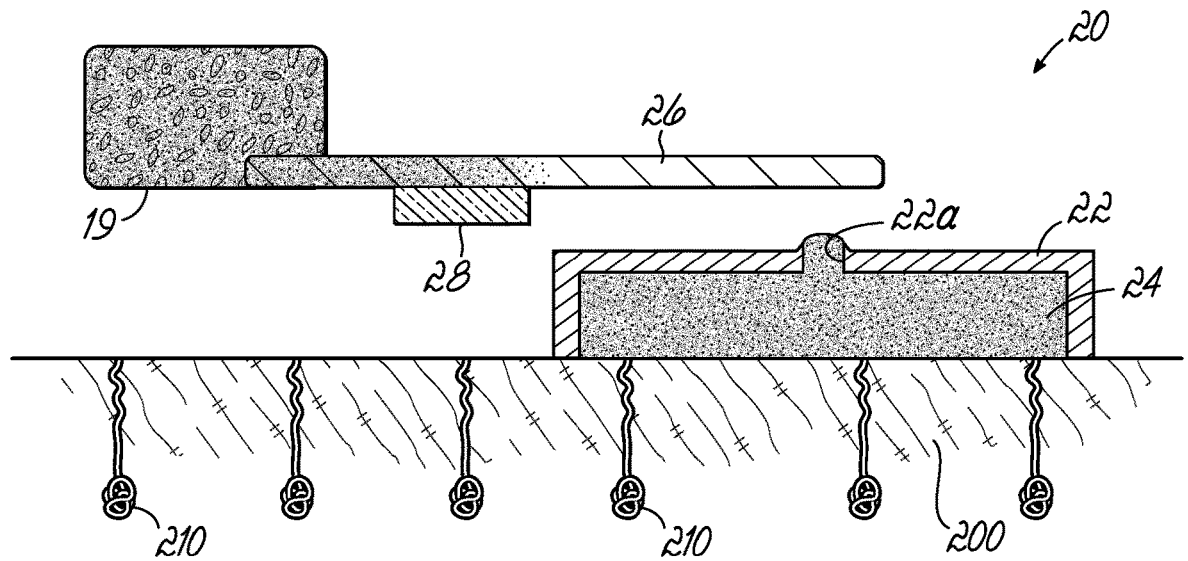
FIG. 5D is a schematic cross-sectional view of the device of FIG. 5A after the discrete sample of fluid has entered the wicking component.

Over time, the biofluid fills the reservoir 24 creating a pressure that forces fluid to begin moving through the opening 22a (FIG. 5B). There may be a hydrophobic medium (e.g., air) between the wicking component 26 and the opening 22a. The fluid pressure from the fluid in the reservoir 24 and the hydrophobicity of the surrounding medium causes the water to bulge out of the opening 22a, forming a droplet. As shown in FIG. 5C, due to capillary forces, the fluid moving through the opening 22a contacts the wicking component 26 before spilling out over the top of the chamber 22. The distance between the wicking component 26 and the opening 22a is determined based on, for example, the properties of the sample fluid and the size of the opening 22a. As the sample of the biofluid travels through the wicking component, the biofluid in the reservoir 24 loses contact with the wicking component 26 (FIG. 5D). As more biofluid enters the reservoir 24, the process is repeated. Thus, the wicking component 26 transports a series of droplets having discrete, quantized volumes of the biofluid across the analyte sensor 28. As with the device 10, the measured current will increase rapidly and then decrease as the analyte in each sample is consumed by the sensor 28 or as it flows away from the sensor 28.

Figure 6:
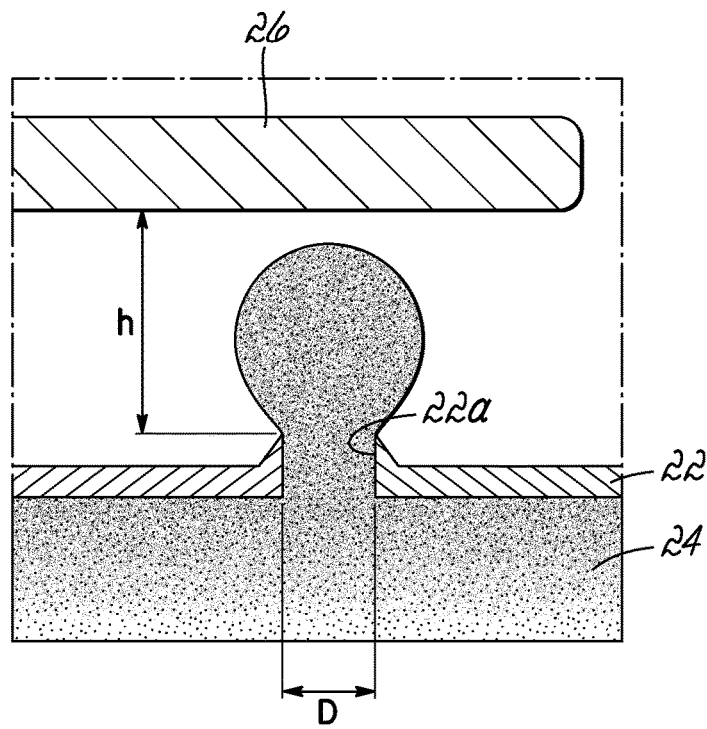
FIG. 6 is an enlarged cross-sectional view of the encircled portion of FIG. 5B.

With reference to FIG. 6, the formation and final volume of the droplet are controlled at least in part by the height (h) of the wicking component 26 relative to the opening 22a and the diameter (D) thereof. To understand the amount of volume that could be dispensed, the droplet is roughly estimated as the volume of a hemisphere $$V = \frac{2}{3}\pi(h)^3$$

(assuming the height and opening are the same size, viz. D=h), the volume could be as small as 1 nL (e.g., for h=0.8 mm) or several hundred of µL 's (e.g., for h>4 mm). For larger heights, the droplet assumes a more spherical shape, depending on the contact angle (θ) of the droplet to the substrate, the volume is Volume=4π/3 r³ (2-3 cos(θ)+ [ cos ]³ (θ))/4.

Each droplet contacts with the wicking component 16, 26 forming a capillary bridge (shown in FIG. 4B), and the capillary bridge must repeatedly break to dispense a series of discrete droplets. For example, the capillary bridge may repeatedly break if (1) the hydrophobicity properties do not change and (2) there is enough input flow resistance to allow a droplet to break away, which can be controlled, for example, by making the supply channel thinner and longer than the droplet chamber or by making the height h larger than the diameter D. Decreasing or increasing either the height h or diameter D will directly affect the volume of the dispensed droplet and frequency of the droplets entering the wicking component 26. A smaller diameter D encourages the droplet capillary bridge to break closer to the inlet which would allow the volume of the droplet to be reduced. Thus, the volume of the droplets and frequency of the sensing may be determined by varying the height h or the diameter D. The diameter D should be at least half the size of the height of the chamber. In order to ensure a consistent droplet volume, the height h of the capillary bridge must be highly reproduceable across devices. Therefore, methods for manufacturing the device may control the height h to within specified tolerances. For example, the height h may be 10, 100, 1000, 2000, or 5000 µm, or any measurement in between, depending on required droplet volume and frequency of droplet formation, with a tolerance of +/−1%, 2%, 10%, or 20%, depending on the requisite flow rate accuracy, or use case. Some embodiments may employ techniques to actively adjust droplet volume, such as having an adjustable height h, or an opening 22a that has an adjustable diameter D.

Figure 16A:
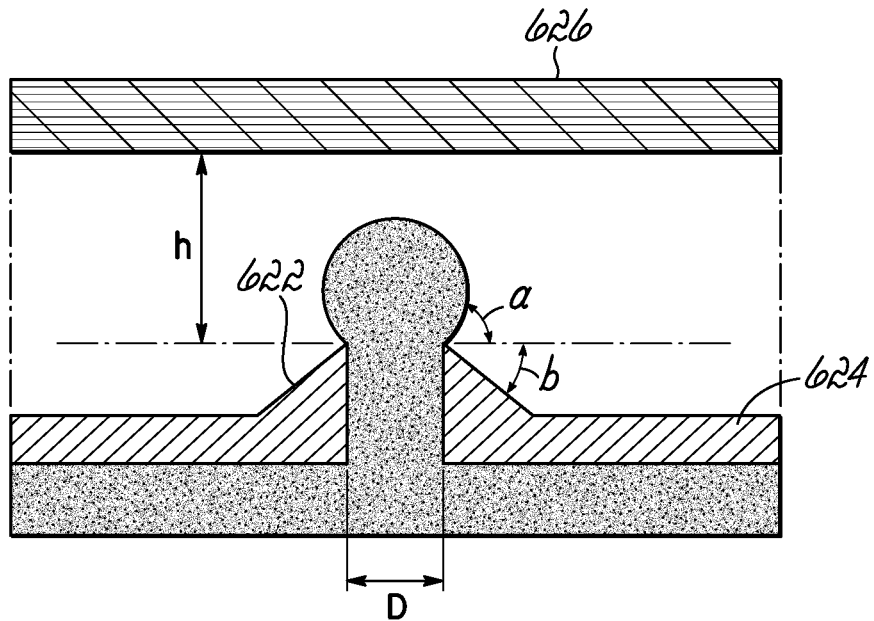
FIG. 16A is an alternative embodiment of the cross-sectional view shown in FIG. 6.
Figure 16B:
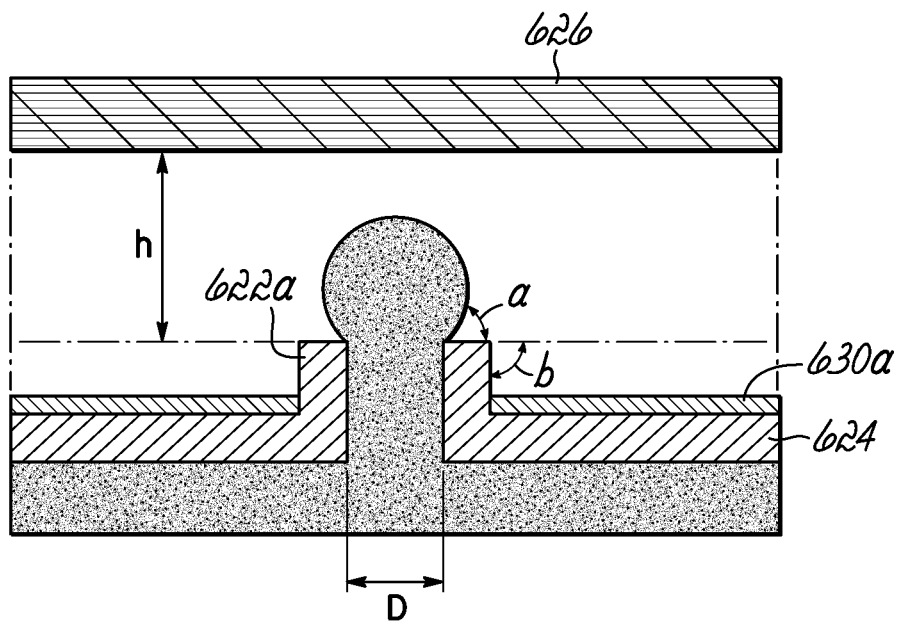
FIG. 16B is an alternative embodiment of the cross-sectional view shown in FIG. 6.

In addition, increasing the hydrophobicity or structure of the chamber 22 and/or opening 22a may also affect the formation and volume of the droplet. For example, the chamber surface surrounding the opening 22a may be treated with a hydrophobic coating, such as Teflon, silica nano-coating, micro- and/or nano-scale roughness treatments, self-cleaning coatings, etc. In another example, shown in FIG. 16A, a chamber 624 includes an angled surface or rim 622 around the opening 22a that increases pinning of the droplet by increasing the potential contact angle between the droplet and the chamber surface 624. In this example, the contact angle is increased from a to (a+b). With reference to FIG. 16B, in another embodiment, the opening 22a is surrounded by a shelf 622a that performs a similar function to that performed by the rim 622 from FIG. 16A.

Due to potential fouling of the surface 620 during operational use, the contact angle between the droplet and the surface will tend to decrease over time, allowing the droplet volume to increase before wetting onto the wick 626. Therefore, in the absence of suitable efforts to control the contact angle between the droplet and the surface, such as those disclosed herein, surface fouling can prevent the formation of droplets of a consistent volume. Other means of reducing the effects of fouling include using antimicrobial coatings on the surface 624, the opening 22a, the wicking component 26, and/or the electrodes (see 130, 132, FIG. 12).

Another important factor for controlling droplet volume consistency is the roughness of the surface 624. As discussed above in the context of hydrophobicity, the substrate's root mean squared roughness values ($R_{RMS}$) has substantial impact on the interaction of the droplet with the surface 624, and hence the droplet volume. Therefore, substrate roughness will need to be controlled to provide consistent device-to-device droplet volume for a given height h and diameter D. Further, substrate roughness may be adjusted based on the selection of substrate materials. For example, the substrate may be a textile, which would have a higher roughness (typically with a mean roughness value>1000 nm), a polymer, such as PET or PVC (RMS roughness>100 nm), or glass or metal, which would have a lower $R_{RMS}$ (<10 nm) depending on the polishing or finishing. A coating (e.g. silica beads or electrodeposited copper on aluminum coated with stearic acid) also will affect $R_{RMS}$. Ideally $R_{RMS}$ for the substrate will be within $R_{RMS}$=100-7000 nm, and device-to-device roughness variation for a given surface 624 material may be controlled to within $R_{RMS}$=10 nm. Roughness is only one parameter of water contact angle. Another parameter of water contact angle may be molecular interaction of the substrate to a water droplet.

Droplet volume control may also be facilitated by maintaining the volume around the opening 22a in a dry state. If biofluid is allowed to pool on the surface 624 near the opening 22a, the contact angle of the substrate would be effectively zero, preventing the formation of a droplet altogether, or causing the droplet to spread out, affecting the consistency of the volume. Various techniques may be used to ensure this critical area is kept in a dry state, such as by including a fluid removal component 630a (shown in FIG. 16B) on the surface 624 around the opening. The fluid removal component 630a may be a desiccant, an absorbent hydrogel, a paper or textile wick, or other suitable material.

Droplet volume may also be affected by acceleration forces on the device. For example, the device may be a sweat sensing device worn on the body, and may be subject to a wide range of variable acceleration forces due to the wearer's activity, such as running, playing contact sports, working in hazardous conditions, operating aircraft or other vehicles, etc. Rapid jarring forces experienced by the wearer could cause the droplet to prematurely detach from the opening, could cause the droplet to wet onto the surrounding surface 624, or could prevent the droplet from reaching the wicking component 26 altogether. Therefore, the device may be configured to withstand or mitigate the effect of acceleration forces on droplet volume. The relationship between droplet surface tension and acceleration forces can be described through the Bond number $$(B_O) = \frac{\Delta\rho a L^2}{\sigma},$$

where Δρ is the density difference between phases (here the droplet and air), a is acceleration, L is characteristic length, and σ is the surface tension of the droplet. These factors may be adjusted to improve droplet resiliency to acceleration forces, chiefly by increasing the surface tension of the droplet. For example, the device may be configured with Bo in the range of 0.00135 (for a droplet radius of 5 μm) which would have a Bo=0.00135, which could withstand 3640 G before becoming unstable (assuming a bond number of 0.5 would make the droplet unstable and calculating for a in the equation described above.

The net effect of such disclosed efforts to control for droplet volume is a biofluid sensing device that is calibrated based on such factors, or ideally is calibration free. To the extent that given h, D, surface roughness, Bo, etc., a device configuration can produce consistent droplet volumes from device-to-device, calibration should not be necessary. Batch calibration at the time of manufacturing may also be required or desirable.

It should be recognized that the embodiments described herein may be applied to mechanisms other than sensing mechanisms. For example, the analyte sensor 18 of the device 10 may be replaced with other devices, reactions, or fluid exchanges that would benefit from discrete volume dispensing of a fluid. In an embodiment, the analyte sensor 18 may be a component that produces a reaction when in contact with a target component of the fluid. For example, the reaction may be observable (e.g., visual, electrical, chemical byproduct, chemiluminescent, etc.), and a flow rate of a biofluid over the sensor 18 could still be calculated directly.

Figure 7:
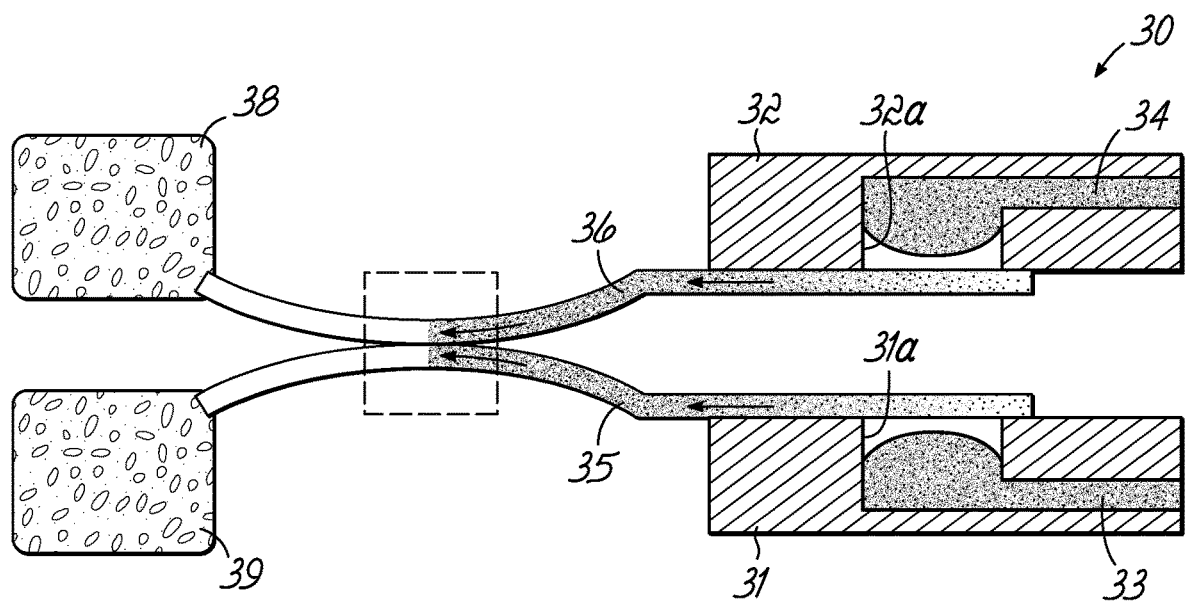
FIG. 7 is a schematic cross-sectional view of a device according to an embodiment of the disclosed invention showing discrete volume dosing of two solutions for a reaction therebetween.

With reference to FIG. 7, in an embodiment, a device 30 that includes two subdevices 31, 32, each of which are capable of discrete volume dosing. Each subdevice 31, 32 includes a fluid-impermeable chamber 33, 34 that includes an opening 31a, 32a and defines a fluid channel 33, 34, which may be coated with a hydrophobic material. The channels 33, 34 are designed to receive a continuous, pressure-driven flow of two sample fluids, solution A and solution B. Solutions A and B travel through their respective channels 33, 34 towards the openings 31a, 32a. Each subdevice 31a, 31b further includes a wicking component 35, 36 at least a portion of which is adjacent to the opening 31a, 32a of the chamber 33, 34. The wicking components 35, 36 are in fluidic contact along a portion thereof. As the solutions A and B travel through the wicking components 35, 36, they come into contact allowing a reaction therebetween. In an embodiment, the reaction of solutions A and B may produce feedback or a signal. Pumps 38, 39 are in fluidic contact with the wicking component 35, 36 and aids in drawing the reacted solutions through the wicking components 35, 36 by capillary forces.

Figure 8A:
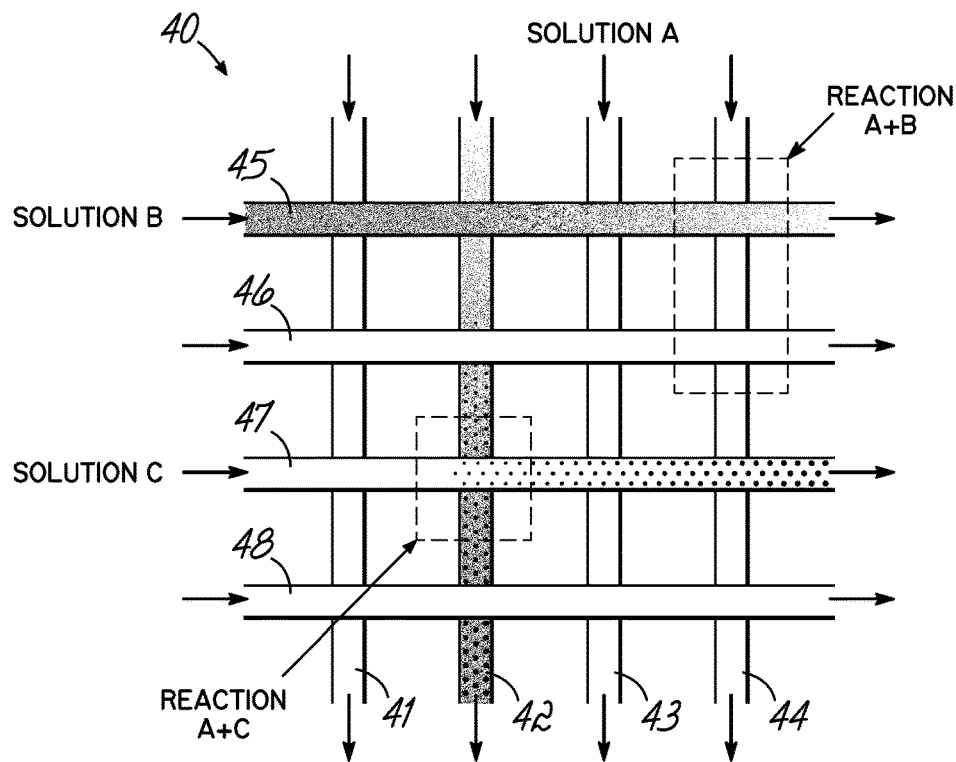
FIG. 8A is a schematic top view of a device according to an embodiment of the disclosed invention showing intersecting wicking channels that form a multiple well assay.
Figure 8B:
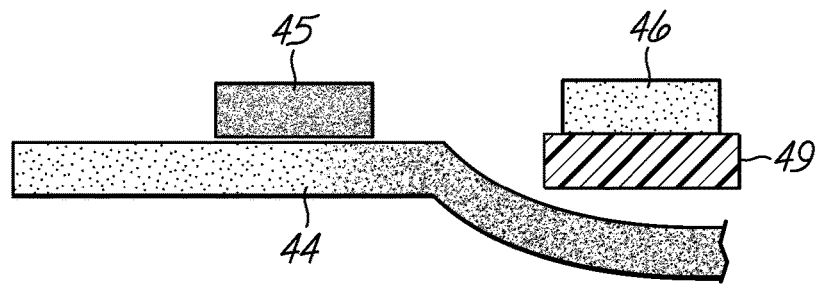
FIG. 8B is a schematic cross-sectional view of the device of FIG. 8A showing a woven configuration of intersecting wicking channels.

With reference to FIGS. 8A and 8B, in an embodiment, a discrete volume dosing system may be used as a programmable multiple well assay 40. Only the wicking components of the discrete volume dosing system are shown for clarity. While a 16-well assay is shown, it should be recognized that the size of the assay may vary. The discrete volume dosing system may produce discrete samples of a known volume onto each wicking component 41, 42, 43, 44, 45, 46, 47, 48. For example, discrete samples of solution A can be dispensed onto wicking components 41, 42, 43, 44, discrete samples of solution B can be dispensed onto wicking components 45, 46, and discrete samples of solution C can be dispensed onto wicking components 47, 48. As the samples of the solutions A, B, and C move through the wicking components 41-48, reactions between the solutions occur when two samples pass through the areas in which the wicking components 41-48 are in fluidic contact with one another. The reactions may provide feedback at the reaction site, and the reacted solution may travel to the end of the respective wicking channel FIG. 8B shows an example woven configuration of the wicking components 44, 45, 46. Wicking components 44, 45 are in fluidic contact with each other, while the wicking component 44 is fluidically isolated from the wicking component 46 due to a barrier 49. Thus, solutions A and B are allowed to react without interference from solution C.

In an aspect of the disclosed invention, a discrete volume dosing system may be programmable and "digital" based on a predefined layout of the wicking components and dispensing patterns. A discrete volume dosing system could be controlled to dispense or not dispense fluid and, based on the array of the wicks, produce digital logic. As an example, the multiple well assay 40 could determine if solution A and solution B are present and indicate a positive. The programmable layout coupled with discrete dispensing creates a digital logic and reprogrammable system.

Figure 9:
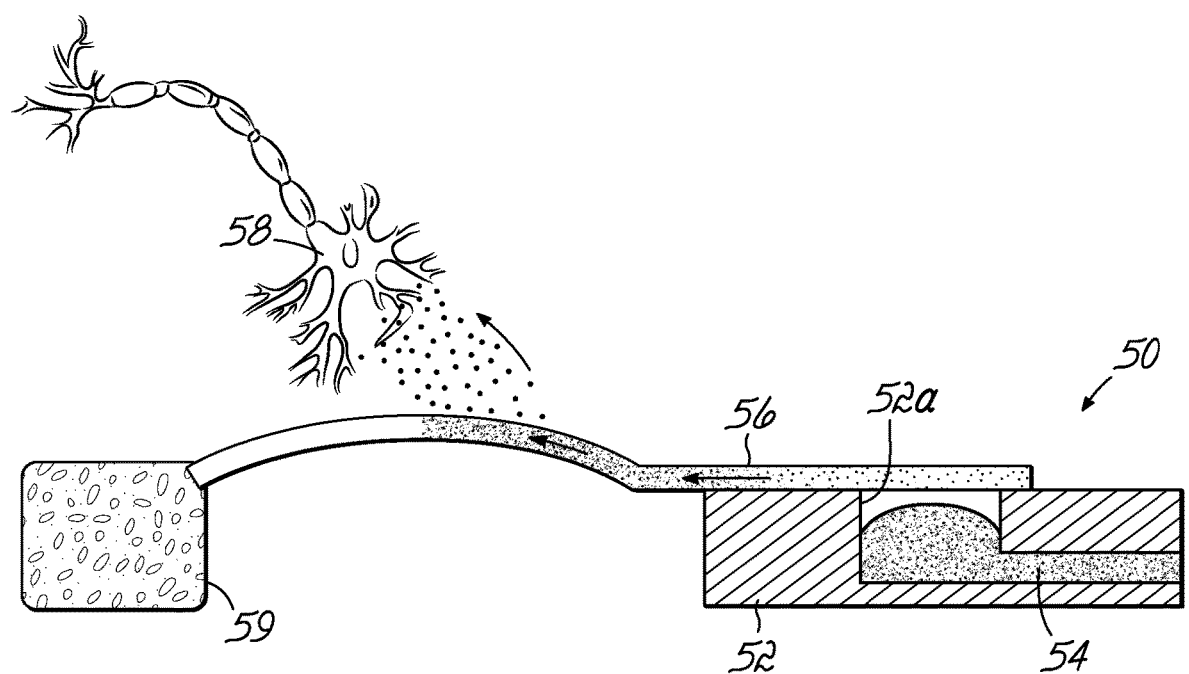
FIG. 9 is a schematic cross-sectional view of a device according to an embodiment of the disclosed invention capable of functioning as a biomimetic artificial nervous system.

With reference to FIG. 9, in an embodiment, a discrete volume dosing system may function as a biomimetic artificial nervous system. A device 50 is configured to transmit neurotransmitters over a long range (e.g., greater than 100 μm). The device 50 includes a fluid-impermeable chamber 52 that includes an opening 52a and defines a fluid channel 54, which may be coated with a hydrophobic material (e.g., Telfon or silica gel). The channel 54 is designed to receive a continuous, pressure-driven flow of a fluid containing neurotransmitters that travels through the channel 54 towards the opening 52a. The device 50 further includes a wicking component 56 (e.g., Rayon fibers, sodium polyacrylate, cellulose, etc.) at least a portion of which is adjacent to the opening 52a of the chamber 52. The wicking component 56 transports fluid from the channel 54 to a neuron 58, which creates an action potential. The neuron 58 or a culture of neurons 58 may be placed adjacent to or grafted into the wicking component 56. A pump 59 is in fluidic contact with the wicking component 56 and aids in drawing the sample fluid through the wicking component 56 and across the neuron 58. Since the neurotransmitters are discretely dispensed, the neuron 58 will not continuously fire. The neuron 58 will only fire when it receives each discrete sample of solution. Thus, an artificial nervous system that mimics a more natural environment (i.e., discrete packets of information), with the added benefit of signaling over a long range via the wicking component 56. Furthermore, similar to the multiple well assay 40, this discrete, quantized dispensing of solution samples introduces "digital logic" into the system. It should be recognized that the discrete volume dosing system may have other applications such as, without limitation, the delivery of nutrients to a cell culture or an in-vitro simulated artificial blood pumping system.

Further, in an embodiment, a discrete volume dosing system may include the electrical pulses described above. For example, electrical pulses may be applied to an analyte sensor (e.g., sensor 18) of a discrete volume dosing system. A combination of these aspects results in a system that is capable of supporting very small sample volumes while retaining the accuracy of the measurements even with a variable or erratic flow rate.

Figure 10A:
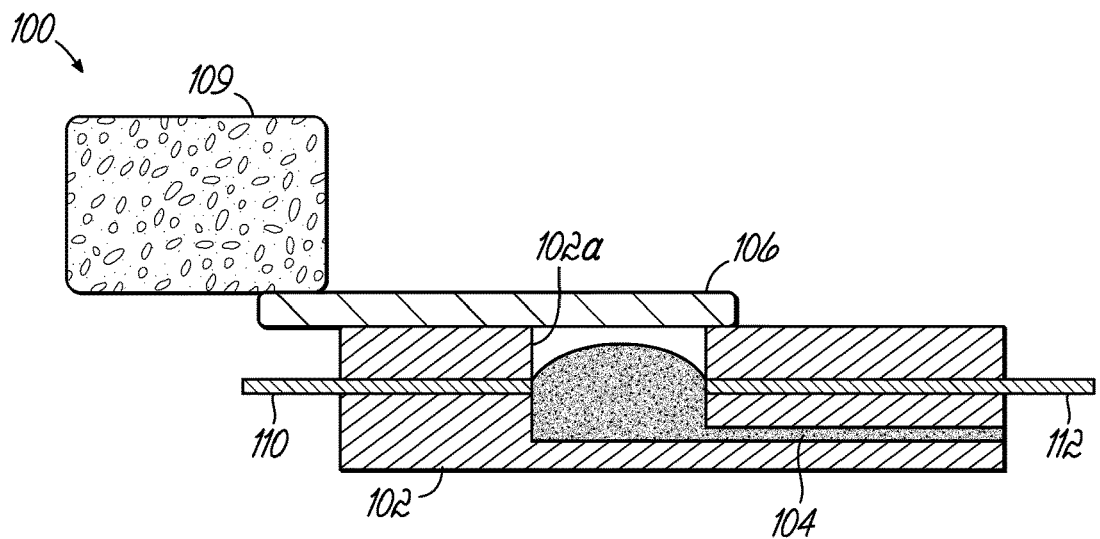
FIG. 10A is a schematic cross-sectional view of a device according to an embodiment of the disclosed invention.
Figure 10B:
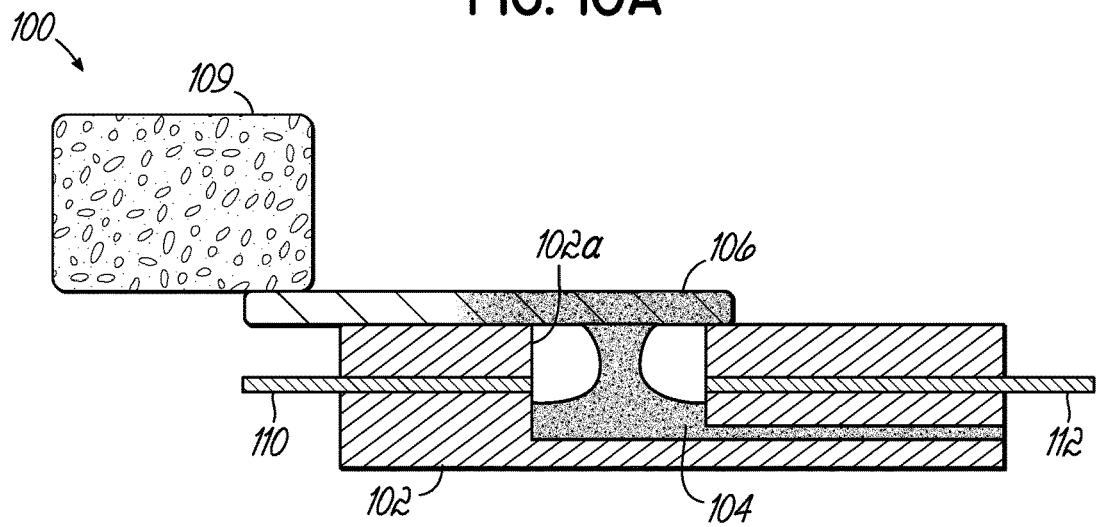
FIG. 10B is a schematic cross-sectional view of the device of FIG. 10A after the fluid contacts the wicking component.
Figure 10C:
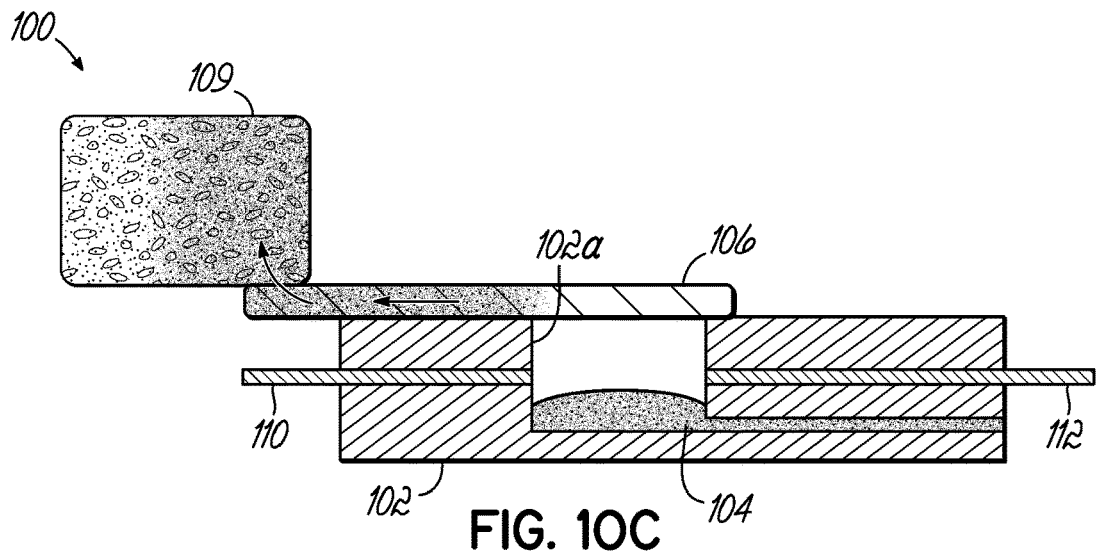
FIG. 10C is a schematic cross-sectional view of the device of FIG. 10A after the discrete sample of fluid has entered the wicking component.

With reference to FIGS. 10A-10C, in an embodiment, a discrete volume dosing system is capable of monitoring the flow rate of the fluid in real time. The discrete volume dosing system comprises a fluid sensing device 100, which is a closed or sealed system in which discrete, quantized samples of fluid are dispensed. The device 100 includes a fluid-impermeable chamber 102 that includes an opening 102a. The chamber 102 may be made of, for example, acrylic. The chamber 102 defines a fluid channel 104, which may be coated with a hydrophobic material (e.g., Teflon or silica nano-coatings). The channel 104 is designed to receive a continuous, pressure-driven flow of sample fluid. The sample fluid travels through the channel 104 towards the opening 102a. The device 100 further includes a wicking component 106 (e.g., Rayon or polyester fibers, sodium polyacrylate, cellulose, etc.) at least a portion of which is adjacent to the opening 102a of the chamber 102. The wicking component 106 transports fluid from the channel 104. A pump 109 is in fluidic contact with the wicking component 106 and aids in drawing the sample fluid through the wicking component 106 and away from the opening 102a. Suitable materials for the pump 109 include sodium polyacrylate or a wicking material. As described above, the device 100 is designed to ensure that the discrete, quantized samples maintain a constant volume.

Figure 11:
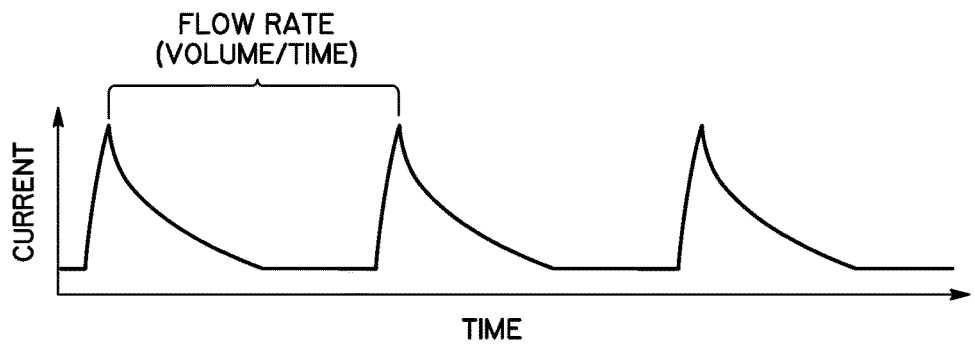
FIG. 11 is a graph of the current over time monitored while droplets are dispensed by the device of FIG. 10A.

The device 100 further includes electrodes 110, 112. The electrodes may be made of, for example, metal or polymer. In the illustrated embodiment, the electrodes 110, 112 are embedded in the chamber 102 and form a part of the wall defining the fluid channel 104. The electrodes 110, 112 are positioned to be in fluidic contact with the fluid sample as it travels through the fluid channel 104 and to the wicking component 106. When there is no fluid between the electrodes 110, 112, the circuit is open. When the fluid contacts both of the electrodes 110, 112 and when a voltage or current is being applied, the electrodes 110, 112 are short-circuited (i.e., the circuit between the electrodes 110, 112 becomes a closed circuit). As the fluid sample separates from the bulk of the fluid and enters the wicking component 106, the circuit between the electrodes 110, 112 opens. In other words, the electrodes 110, 112 are in the path of the droplet formation and, as each discrete sample moves through the opening 102a, the circuit between the electrodes 110, 112 cycles from an open circuit, to a short circuit, and back to an open circuit, which creates discrete spikes in the current. By measuring the current during the repeated short-circuiting, the frequency of dispensing can be monitored and recorded. An example of the current response to short-circuiting cycles is shown in FIG. 11. Because the volume of each sample is known (or estimated), the flow rate may be determined based on the volume of each sample and the time between current or voltage spikes.

Figure 12:
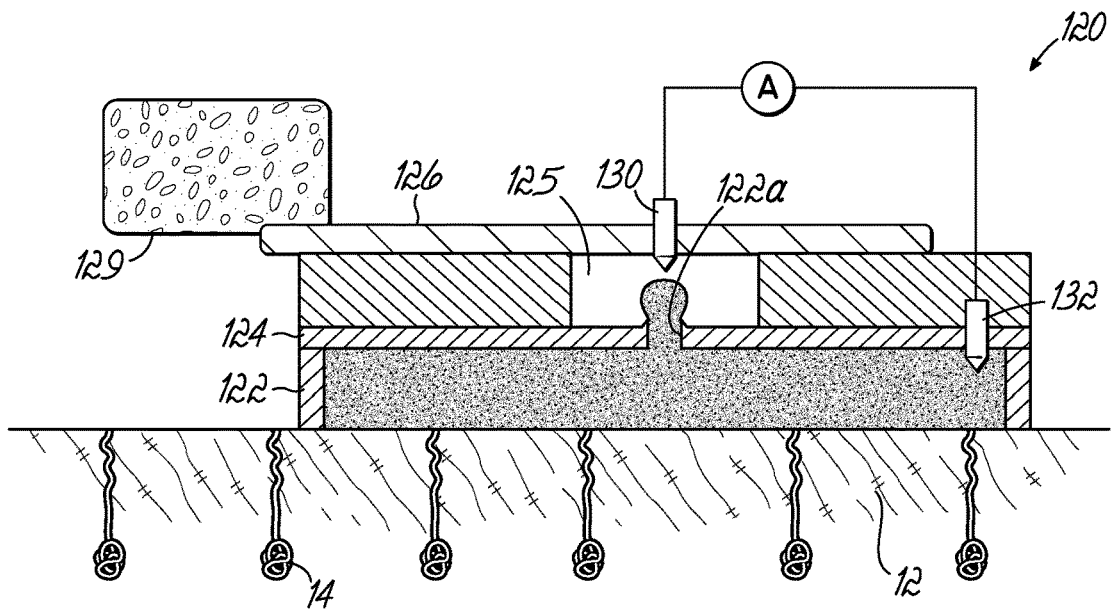
FIG. 12 is a schematic cross-sectional view of a device according to an embodiment of the disclosed invention.

The positions of the electrodes within the discrete volume dosing system may vary (e.g., in the channel; in the outlet; in or on the substrate, or a combination of any of these). With reference to FIG. 12, in an embodiment, a discrete volume dosing system is capable of monitoring the flow rate of the fluid in real time comprises a biofluid sensing device 120, which is a closed or sealed system in which discrete, quantized samples of fluid are delivered and analyzed independent of flow rate. The device 120 is positioned on skin, which includes sweat ducts. The device 120 includes a first fluid-impermeable chamber 122 that includes an opening 122a. The chamber 122 may be made of, for example, acrylic. The chamber 122 defines a fluid channel 124, which may be coated with a hydrophobic material (e.g., Teflon or silica nano-coatings). The channel 124 is designed to receive a continuous, pressure-driven flow of sample fluid. The sample fluid travels through the channel 124 towards the opening 122a. A portion of the fluid flows through the opening 122a into a second fluid-impermeable chamber 125. The device 120 further includes a wicking component 126 (e.g., Rayon or polyester fibers, sodium polyacrylate, cellulose, etc.) at least a portion of which is adjacent to the second chamber 125.

One or more optional pumps 129 is in fluidic contact with the wicking component 126 and aids in drawing the sample fluid through the wicking component 126 and away from the second chamber 125. In this and other embodiments herein, the pump size or capacity may be selected to correspond to expected biofluid throughput of the device application. For example, a sweat sensing device may include a pump 129 with capacity based on the expected sweat generation rates, including the maximum instantaneous sweat rate, for the device wearer's activity. A device worn for active perspires may therefore require a larger pump capacity than for a sedentary wearer. The duration of the device application also will affect the amount of biofluid the pump will be required to absorb. Other factors, such as clearance rates for wicking biofluid through and out of the wick may also be considered. Pump capacity may be for example, 100 µL for short duration (about 30 minutes of active sweating) applications, to 20 mL for extended wear applications. For a wearer sweating at 5 µL/min/cm$^2$, this latter pump volume would allow for approximately 24 hours of collection time. Other embodiments may include a waste outlet (not shown) and/or waste reservoir (not shown) in fluidic communication with the wick or optional pump. The waste outlet would allow excess biofluid to move out of the device, increasing biofluid throughput capacity. The pump 129 could allow for evaporation extending the collection time beyond 24 hours. Similarly, a waste reservoir would collect excess biofluid and store it until the device application was complete. Reservoir capacity may similarly depend on expected device biofluid throughput and may be determined in conjunction with pump and/or wick capacity.

The device 120 further includes a first electrode 130 positioned so that it contacts each droplet that passes through the second chamber 125 and into the wicking component 126. A second electrode 132 is in contact with the fluid in the fluid channel 124. When there is no fluid droplet passing through the second chamber 125 (i.e., that is still in contact with the bulk of the fluid in the fluid channel 124), the circuit is open. When the fluid droplet contacts the electrode 130 and is still in contact with the bulk of the fluid in the fluid channel 124 and when a voltage or current is being applied, the electrodes 130, 132 are short-circuited (i.e., the circuit between the electrodes 130, 132 becomes a closed circuit). As the fluid sample separates from the bulk of the fluid and enters the wicking component 126, the circuit between the electrodes 130, 132 opens. In other words, the electrode 130 is in the path of the droplet formation and, as each discrete sample moves through the opening 122a, the circuit between the electrodes 130, 132 cycles from an open circuit, to a short circuit, and back to an open circuit, which creates discrete spikes in the current. As described above, the frequency of dispensing can be monitored and recorded, and the flow rate may be determined based on the volume of each sample and the time between current or voltage spikes.

Such real-time flow rate monitors have applications in, for example, sweat rate monitoring or lab-on-chip channels. Depending on the application, the parameters of the device may be adjusted to ensure discrete samples or droplets may be formed and monitored. Each parameter in the device (e.g., aperture and height) controls the operational flow rate range at which the device can operate and may be adjusted for the intended application. For example, low flow rates (e.g., less than µL/min) may require a smaller droplet so that the frequency of dispensing is in an acceptable range for the application (i.e., f<min$^{-1}$). Likewise, larger flow rates (e.g., greater than μL/min) may require larger droplets to decrease the frequency of dispensing.

The electrodes 130, 132 can be various conducting materials such as tungsten wire, a gold sputtered substrate, or a metal coated nylon mesh. The wicking component 126 is some wicking substrate. The electrodes' 130, 132 mesh is important for the current sampling rate because during operation of the device 120, the biofluid goes through the mesh, not around, to get to the substrate. A water layer that is formed is on the substrate and in the mesh. This may allow for a longer time to sample the current spike. When the first droplet is dispensed the electrodes 130, 132 and mesh are dry, causing the droplet to touch the electrodes 130,132 and continue to grow until the droplet overcomes surface tension and breaks onto the wicking component 126. Once the first droplet breaks and wets the wire mesh, the volume of the droplet becomes lower and steadier. The droplet touches the water layer on the wire mesh which breaks the droplet quickly because of cohesion. If the substrate is wetted this occurs. If the substrate dries, the droplet behaves like the first droplet. The volume of the droplet has been seen to change in volume over time, either because of the expansion of the substrate or the expansion of the water layer.

Alternatively, the electrodes 130, 132 may be gold coated Rayon. The droplets broke onto the wicking component 126 much faster than when alternative electrode materials were used at least because of the high wicking strength of the Rayon. Electrodes 130, 132 including gold coated Rayon do not need to stay wet (unlike the mesh electrode), however, such electrodes 130, 132 require a faster sampling rate, which is not always possible.

Figure 15A:
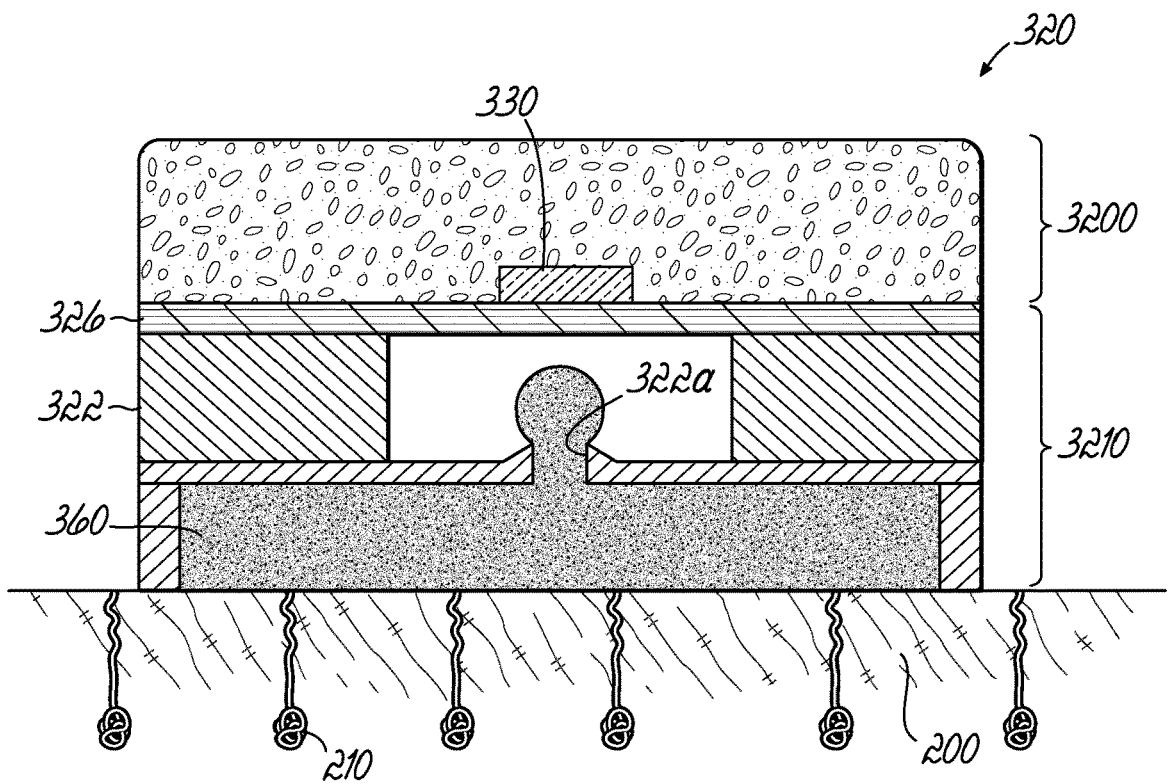
FIG. 15A is a schematic cross-sectional view of a device according to an embodiment of the disclosed invention.
Figure 15B:
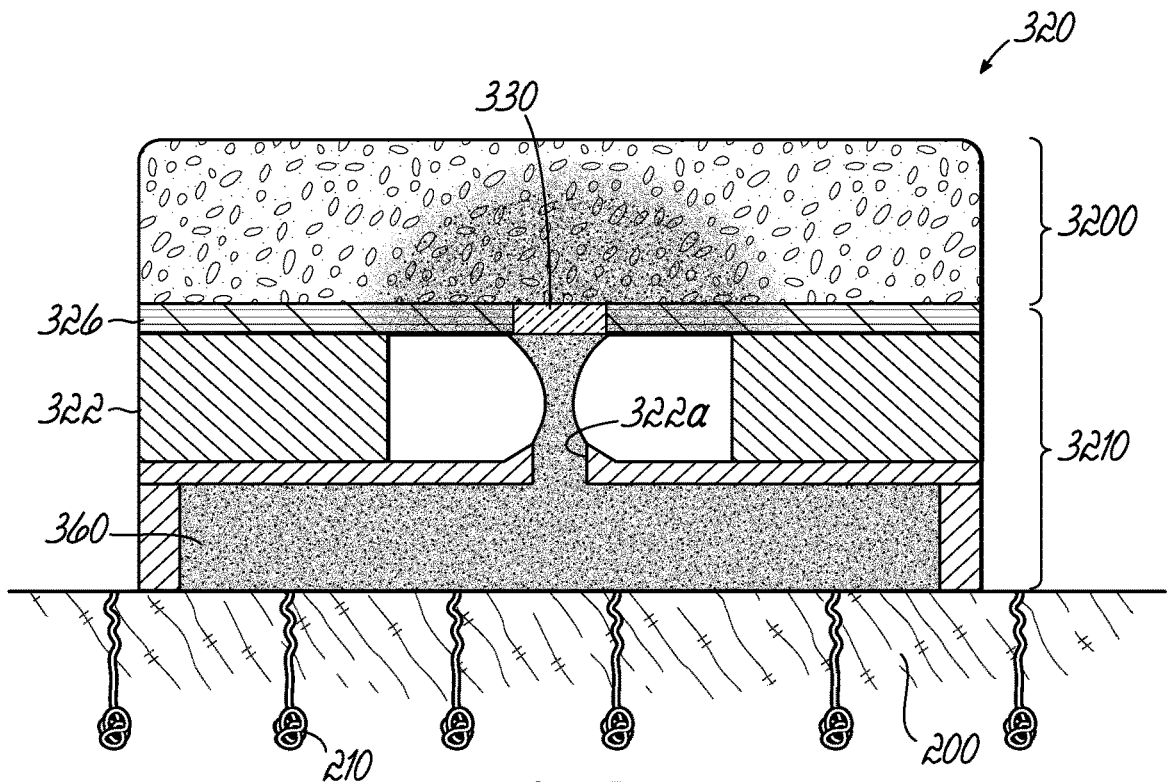
FIG. 15B is a schematic cross-sectional view of a device according to an embodiment of the disclosed invention.

Various embodiments of the disclosed invention may benefit from modular configurations that include reusable and disposable components. For example, electronic components may represent a substantial portion of the cost of a device, and further may be robust enough to endure several device use cycles. Such components may be ideally placed in a reusable module. By contrast, microfluidic components, certain sensor types, skin interface components, e.g., adhesives, may be single-use or limited-use components appropriate for a disposable module. With reference to FIG. 15A, a device 320 of the disclosed invention is depicted with a reusable module 3200 and a disposable module 3210. The reusable module 3200 includes, among other components, one or more electrodes 330, and supporting electronics. The disposable module 3210 includes, among other components, a microfluidic wick 326, a substrate 322, and an opening 322a. With reference to FIG. 15B, in an alternate embodiment of a modular device, the one or more electrodes 330 is located in the microfluidic wick 326, and hence in the disposable module 3210. In another embodiment, the microfluidic wick 326 includes the electrode, as shown in FIG. 15B. As shown in FIGS. 15A and 15B, the reusable module 3200 or the disposable module 3210 can be positioned on skin 200 to sample sweat produced by sweat glands 210. It is important to note that the second electrode is positioned in contact with the fluid 360 or the skin 200, which is not shown in the FIGS. 15A and 15B.

Figure 13:
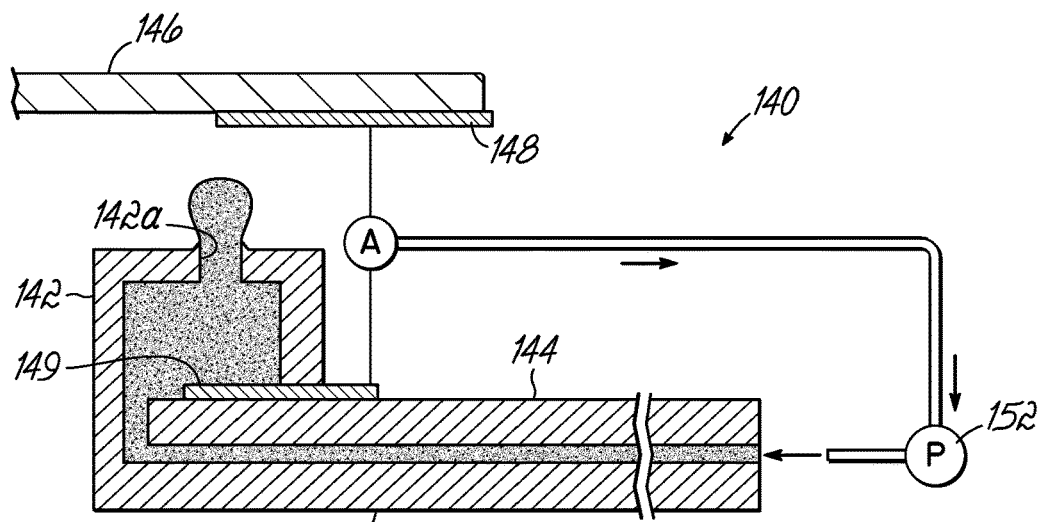
FIG. 13 is a schematic cross-sectional view of a device according to an embodiment of the disclosed invention.

In an aspect of the disclosed invention, a device capable of measuring conductivity is coupled to a separate device and is used in a feedback system. For example, the feedback system may be used where a certain volume or flow rate is needed in the connected device or to trigger an action or event in the connected device (e.g., to control a valve). With reference to FIG. 13, in an embodiment, a device 140 is attached to the outlet of a microfluidic device 150 (e.g., a lab-on-chip device) including an input pump 152. The device 140 includes a fluid-impermeable chamber 142 having an opening 142a. The chamber 142 defines at least a portion of a fluid channel 144, which is in fluid communication with the microfluidic device 150. The sample fluid travels from the microfluidic device 150, through the channel 144 towards the opening 142a. Droplets exit the opening 142a and enter a wicking component 146. A first electrode 148 is coupled to the wicking component 146 and contacts each droplet as they enter the wicking component 146. A second electrode 149 is in contact with the fluid in the fluid channel 144. A controller monitors the current or voltage spikes over time to determine the frequency of dispensing and the flow rate. These measurements are used as feedback to control the input pump 152. For example, the measured flow rate would provide feedback to the input pump 152 to dispense the desired fluid volume to the microfluidic device 150. In another embodiment, the device 150 may be downstream from the discrete volume dosing system 140, and the feedback may be used to control, for example, dispensing applications.

Figure 14A:
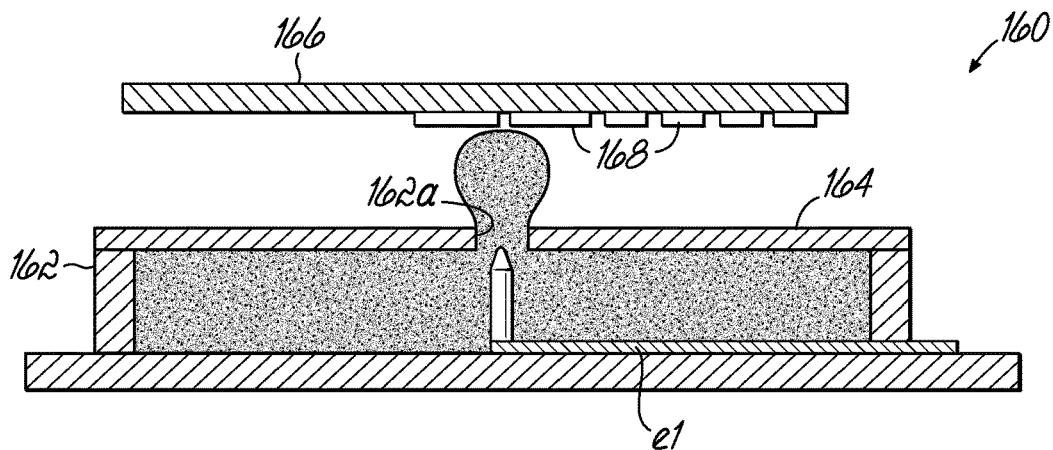
FIG. 14A is a schematic cross-sectional view of a device according to an embodiment of the disclosed invention.
Figure 14B:
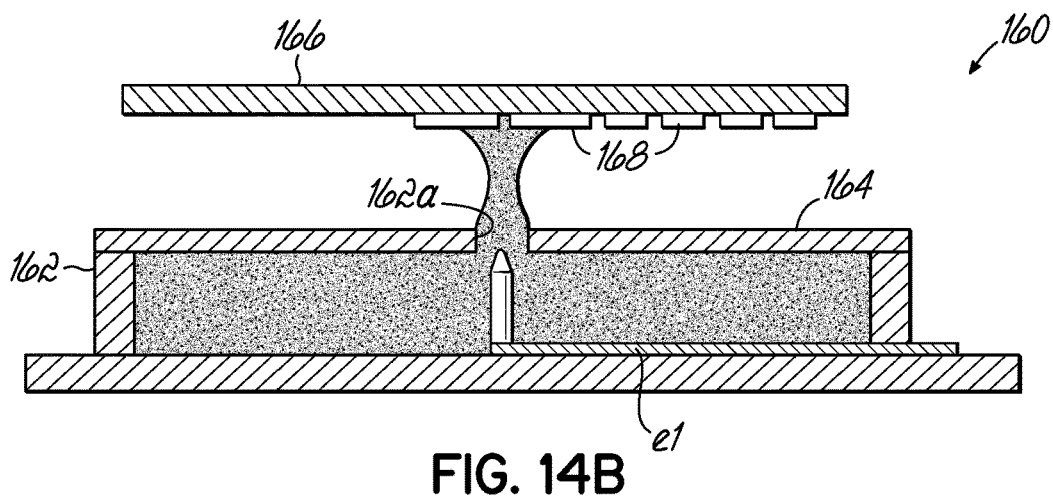
FIG. 14B is a schematic cross-sectional view of the device of FIG. 14A after the fluid contacts the substrate and electrode array.
Figure 14C:
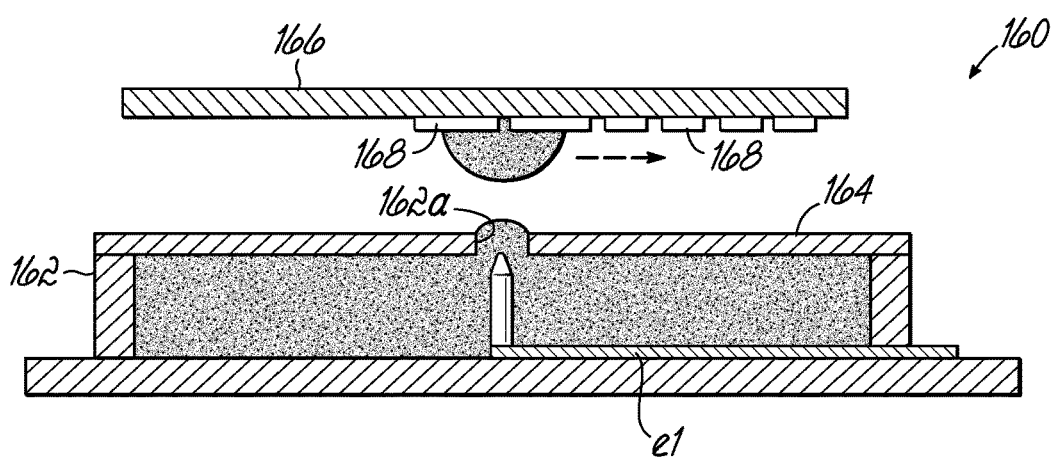
FIG. 14C is a schematic cross-sectional view of the device of FIG. 14A after the discrete sample of fluid has separated from the bulk of the fluid.

With reference to FIGS. 14A-14C, in an embodiment, a discrete volume dosing system that is capable of using active droplet formation and dispensing to monitor the flow rate of the fluid in real time using electrowetting is shown. This may be desirable where it is impossible or not desirable to use a wicking component as a substrate or when more control is required over the droplet formation. In this case, electrowetting is another technique to dispense the droplet and monitor flow rate. The discrete volume dosing system comprises a fluid sensing device 160, which is a closed or sealed system in which discrete, quantized samples of fluid are delivered. The device 160 includes a fluid-impermeable chamber 162 that includes an opening 162a. The chamber 162 defines a fluid channel 164, which may be coated with a hydrophobic material. The channel 164 is designed to receive a continuous, pressure-driven flow of sample fluid. A first electrode e1 is positioned within the fluid channel 164 and is adjacent the opening 162a. The sample fluid travels through the channel 164 towards the opening 162a. The device 160 further includes a substrate 166 at least a portion of which is adjacent to the opening 162a of the chamber 162. The substrate 166 includes an electrode array 168. The electrode array 168 includes two electrodes e2, e3 that are positioned opposite the opening 162a. As a droplet extends from the opening 162a, a high voltage is applied between the electrode e1 (e.g., the anode) and the electrodes e2, e3 (e.g., the cathode). Through electrowetting, the droplet wets the surface and breaks away from the opening 162a from inertial forces of the droplet wetting the surface of the substrate 166. Accordingly, the device 160 is designed to remove discrete, quantized samples from the bulk of the fluid based on the timing of the voltage application. The electrode array 168 includes further electrodes e4, e5, e6, e7 that are spaced progressively further away from the opening 162a. The droplet is translated away from the opening 162a via digital microfluidics (digital electrowetting) between electrodes e2 through e7 (and onward), and the process can be repeated. Of note, this is an active transport method compared to the passive transport method described, for example, in the device 100. In another embodiment, a droplet could make contact between electrodes e1, e2 and an actuator (e.g., a piezoelectric actuator; not shown) located inside the channel 164 would inject a droplet onto the substrate 166 similar to inkjet principals. The droplet, again, could be carried away by digital microfluidics.

EXPERIMENTAL DATA

Devices were fabricated with different thicknesses and compared to the theoretical and measured volumes of the droplets and the standard deviation of each device was calculated. Table 1 shows their results.

TABLE 1

| Experiment | Thickness (mm) | Theoretical Volume (nL) | Averaged Measured Volume (nL) | Standard Deviation of each device (nL) |
|---|---|---|---|---|
| 180604-1-4 .5 | 0.447 | 46.76502725 | 150.516667 | 6.178371414 |
| 180620-1-1 .5 | 0.447 | 46.76502725 | 135.83672 | 5.145319869 |
| 180614-4-2 .5 Post | 0.447 | 46.76502725 | 98.2662037 | 1.458667762 |
| 180518 | 0.664 | 153.2861302 | 138.883333 | 2.496849867 |
| 180521 | 0.664 | 153.2861302 | 197.683333 | 1.756733079 |
| 180524-1.5-1 | 0.664 | 153.2861302 | 154.115385 | 1.366235898 |
| 180525 | 0.664 | 153.2861302 | 176.373333 | 3.857433729 |
| 180531-1-1 | 0.664 | 153.2861302 | 215.576389 | 7.658474825 |
| 180531-2-1 | 0.664 | 153.2861302 | 276.177778 | 8.352450295 |
| 180607-1-1 1.5 | 0.951 | 450.3396367 | 473.3125 | 9.134955973 |
| 180608 | 0.951 | 450.3396367 | 505.166667 | 11.40831435 |
| 180612 | 0.951 | 450.3396367 | 494.694444 | 4.449990339 |
| 180604-1-3 | 1.168 | 834.3094267 | 878.041667 | 29.9990172 |
| 180604-1-2 | 1.168 | 834.3094267 | 843.533333 | 28.40607085 |
| 180607 | 1.168 | 834.3094267 | 1146.5 | 24.31940648 |
| 180620-1-4 | 1.168 | 834.3094267 | 623.008333 | 11.49431623 |

Table 1 shows standard deviation calculations for calibration tests.

With droplets of such a small volume, gravity has little to no effect on the volume of the droplet. Experiments designed to test the orientation of the outlet demonstrated that the volume of the droplet is not affected by the orientation. Each droplet maintains an extremely consistent volume (most calibration values result in percent error less than 3.6%) regardless of orientation (i.e. no gravity effects) even over a long period of time (200+ hours).

While specific embodiments have been described in detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

The subject-matter of the disclosure may also relate, among others, to the following aspects:

1. A device, comprising:
   a chamber including a channel and an opening, wherein the channel is in fluidic communication with the opening;
   a wicking component positioned proximate to the opening, wherein the wicking component is configured to receive an amount of biofluid from the channel; and
   a sensor configured to measure a characteristic of an analyte in the biofluid, wherein the sensor is in fluidic communication with the wicking component, and wherein the wicking component is configured to contact the sensor with the amount of biofluid.
2. The device of aspect 1 further comprising a pump, wherein the pump is in fluidic communication with the wicking component, and wherein the pump is configured to promote contact between the amount of biofluid and the sensor.
3. The device of aspect 2, wherein the pump is configured to absorb the amount of biofluid after the amount of biofluid contacts the sensor.
4. The device of any of aspects 1 to 3 wherein the wicking component is positioned no more than 1 cm from the opening and no less than 1 μm from the opening, and has a diameter of no more than 1 cm and no less than 1 μm.
5. The device of aspect 1, wherein the amount of biofluid is independent of a flow rate of fluid in the channel.
6. The device of any of aspects 1 to 5, wherein the amount of biofluid fluid forms a droplet, wherein the droplet has a convex meniscus when received by the wicking component.
7. The device of any of aspects 1 to 6, wherein the channel is coated with a hydrophobic material.
8. The device of any of aspects 1 to 7, wherein the chamber includes a surface treatment around the opening.
9. The device of aspect 8, wherein the surface treatment includes one of the following: an angled rim; a raised shelf; a hydrophobic coating; and an antimicrobial coating.
10. A system comprising:
    a chamber including a channel and an opening, the channel in fluid communication with the opening,
    a wicking component positioned adjacent to the opening configured to receive an amount of fluid from the channel, the fluid including neurotransmitters; and
    a neuron positioned adjacent the wicking component, the neuron configured to detect the neurotransmitters in the fluid in the wicking component.
11. A system comprising:
    a plurality of wicking components;
    a first device comprising:
       a first chamber including a first channel and a first opening, the first channel in fluid communication with the first opening;
       a first wicking component positioned adjacent to the first opening configured to receive an amount of a first fluid from the first channel; and
    a second device comprising:
       a second chamber including a second channel and a second opening, the second channel in fluid communication with the second opening;

a second wicking component positioned adjacent to the second opening configured to receive an amount of a second fluid from the second channel,
wherein the first wicking component is in fluid communication with the second wicking component such that the first amount of fluid and the second amount of fluid are configured to contact each other via the first wicking component and the second wicking component.

12. The system of aspect 11, wherein the first device further comprises a first pump and the second device further comprises a second pump, the first pump is configured to drive the first fluid through the first wicking component and the second pump is configured to drive the second fluid through the second wicking component.

13. The system of any of aspects 11 to 12, wherein the contact of the first fluid and the second fluid is configured to produce a measurable signal.

14. The system of any of aspects 11 to 13, wherein the plurality of wicking components are arranged in an assay such that each of the wicking components contacts each other wicking component.

15. A device, comprising:
a chamber including a channel and an opening, wherein the channel is in fluidic communication with the opening, and wherein the channel and the opening have a hydrophobic coating;
a wicking component configured to receive an amount of biofluid from the opening, wherein the amount of biofluid forms a droplet; and
a plurality of electrodes, wherein each electrode is configured to form a closed circuit when the electrode is in contact with the droplet, and to form an open circuit when the electrode is not in contact with the droplet.

16. The device of aspect 15, wherein the electrodes are configured to detect a flow rate of biofluid through the channel.

17. The device of any of aspects 15 to 16, wherein the electrodes are in fluidic communication with the channel.

18. The device of any of aspects 15 to 17, wherein a first electrode is in fluidic communication with the wicking component and a second electrode is in fluidic communication with the channel.

19. The device of any of aspects 15 to 18, further comprising a pump and a feedback controller, wherein the pump is in fluidic communication with the channel, and wherein the feedback controller is configured to cause the pump to change a flow rate of a biofluid.

20. The device of any of aspects 15 to 19, further including a plurality of electrowetting electrodes, wherein the electrowetting electrodes are in fluidic communication with the wicking component, and wherein the electrowetting electrodes are configured to transport a biofluid in the wicking component.

What is claimed is:

1. A device, comprising:
a chamber including a channel and an opening, wherein the channel is in fluidic communication with the opening;
a wicking component positioned proximate to the opening, wherein the wicking component is configured to receive an amount of biofluid from the channel; and
a sensor configured to measure a characteristic of an analyte in the biofluid, wherein the sensor is in fluidic communication with the wicking component, and wherein the wicking component is configured to contact the sensor with the amount of biofluid, and
wherein the wicking component is positioned no less than 1 μm from the opening.

2. The device of claim 1 further comprising a pump, wherein the pump is in fluidic communication with the wicking component, and wherein the pump is configured to promote contact between the amount of biofluid and the sensor.

3. The device of claim 2, wherein the pump is configured to absorb the amount of biofluid after the amount of biofluid contacts the sensor.

4. The device of claim μ wherein the wicking component is positioned no more than 1 cm from the opening, and has a diameter of no more than 1 cm and no less than 1 μm.

5. The device of claim 1, wherein the amount of biofluid is independent of a flow rate of fluid in the channel.

6. The device of claim 1, wherein the amount of biofluid fluid forms a droplet, wherein the droplet has a convex meniscus when received by the wicking component.

7. The device of claim 1, wherein the channel is coated with a hydrophobic material.

8. The device of claim 1, wherein the chamber includes a surface treatment around the opening.

9. The device of claim 8, wherein the surface treatment includes one of the following: an angled rim; a raised shelf; a hydrophobic coating; and an antimicrobial coating.

* * * * *

UNITED STATES PATENT AND TRADEMARK OFFICE
CERTIFICATE OF CORRECTION

PATENT NO. : 11,524,290 B2
APPLICATION NO. : 16/649211
DATED : December 13, 2022
INVENTOR(S) : Jessica Francis et al.

It is certified that error appears in the above-identified patent and that said Letters Patent is hereby corrected as shown below:

On the Title Page

Column 2, item (57) Abstract, Line 4, change "opening the channel" to --opening, the channel--.

In the Specification

Column 3, Line 66, change "skin" to --device--.

Column 8, Line 9, change "values" to --value--.

Column 8, Line 23, change "$R_{RMS}$ Ideally" to --$R_{RMS}$, Ideally--.

Column 9, Line 6, change "above." to --above).--.

Column 9, Lines 27-28, change "30 that includes two subdevices 31, 32, each of which are" to --30 includes two subdevices 31, 32, each of which is--.

Column 9, Line 45, change "component 35, 36 and aids" to --components 35, 36, and aid--.

Column 9 Line 67, change "channel FIG." to --channel. FIG.--.

Signed and Sealed this
Eighteenth Day of April, 2023

Katherine Kelly Vidal
*Director of the United States Patent and Trademark Office*